United States Patent
Basta et al.

(10) Patent No.: US 10,342,461 B2
(45) Date of Patent: Jul. 9, 2019

(54) METHOD OF GAIT EVALUATION AND TRAINING WITH DIFFERENTIAL PRESSURE SYSTEM

(71) Applicant: ALTERG, INC., Fremont, CA (US)

(72) Inventors: Steven L. Basta, Menlo Park, CA (US); Clifford T. Jue, Santa Cruz, CA (US); Mark A. Shughart, Palo Alto, CA (US); Michael E. Duffy, Sebastopol, CA (US)

(73) Assignee: AlterG, Inc., Fremont, CA (US)

( * ) Notice: Subject to any disclaimer, the term of this patent is extended or adjusted under 35 U.S.C. 154(b) by 205 days.

(21) Appl. No.: 14/769,111

(22) PCT Filed: Mar. 14, 2014

(86) PCT No.: PCT/US2014/029578
§ 371 (c)(1),
(2) Date: Aug. 20, 2015

(87) PCT Pub. No.: WO2014/153201
PCT Pub. Date: Sep. 25, 2014

(65) Prior Publication Data
US 2016/0007885 A1    Jan. 14, 2016

Related U.S. Application Data

(60) Provisional application No. 61/785,317, filed on Mar. 14, 2013.

(51) Int. Cl.
*A61B 5/00* (2006.01)
*A61B 5/11* (2006.01)
(Continued)

(52) U.S. Cl.
CPC ............ *A61B 5/112* (2013.01); *A61B 5/1038* (2013.01); *A61B 5/222* (2013.01); *A61B 5/742* (2013.01);
(Continued)

(58) Field of Classification Search
CPC ....... A61B 5/112; A61B 5/222; A61B 5/1038; A61B 5/742; A61B 2503/10;
(Continued)

(56) References Cited

U.S. PATENT DOCUMENTS

| 32,109 A | 4/1861 | DeBrame |
| 43,972 A | 8/1864 | Coldwell |

(Continued)

FOREIGN PATENT DOCUMENTS

| CA | 2216216 A | 5/1999 |
| CN | 2034152 U | 3/1989 |

(Continued)

OTHER PUBLICATIONS

Montion Control Tips; (retrieved from the internet: www.motioncontroltips.com/lead-screws/); 5 pgs; on Dec. 19, 2016.
(Continued)

*Primary Examiner* — Sundhara M Ganesan
(74) *Attorney, Agent, or Firm* — Shay Glenn LLP

(57) ABSTRACT

There is described an integrated unweighted gait training system having an unweighting system comprising a computer controller; a gait measurement system in communication with the controller; and a display in communication with the computer controller adapted and configured to provide real-time feedback to a user of the integrated unweighting gait training system. The unweighting system may be a differential air pressure (DAP) unweighting system or a non-DAP unweighting system.

32 Claims, 28 Drawing Sheets

(51) Int. Cl.

| | | |
|---|---|---|
| A61B 5/22 | (2006.01) | |
| A61N 1/36 | (2006.01) | |
| A61B 5/103 | (2006.01) | |
| A63B 22/02 | (2006.01) | |
| A63B 22/04 | (2006.01) | |
| A63B 22/06 | (2006.01) | |
| A63B 69/00 | (2006.01) | |
| A63B 71/06 | (2006.01) | |
| G06F 19/00 | (2018.01) | |
| G09B 19/00 | (2006.01) | |

(52) U.S. Cl.
CPC .......... *A63B 22/02* (2013.01); *A63B 22/0235* (2013.01); *A63B 71/0622* (2013.01); *G06F 19/3481* (2013.01); *G09B 19/0038* (2013.01); *A61B 5/486* (2013.01); *A61B 2503/10* (2013.01); *A61B 2505/09* (2013.01); *A61B 2562/0219* (2013.01); *A61N 1/36003* (2013.01); *A63B 22/0242* (2013.01); *A63B 22/04* (2013.01); *A63B 22/0605* (2013.01); *A63B 22/0664* (2013.01); *A63B 69/0028* (2013.01); *A63B 2071/065* (2013.01); *A63B 2071/0625* (2013.01); *A63B 2071/0655* (2013.01); *A63B 2213/004* (2013.01); *A63B 2220/13* (2013.01); *A63B 2220/18* (2013.01); *A63B 2220/30* (2013.01); *A63B 2220/36* (2013.01); *A63B 2220/40* (2013.01); *A63B 2220/51* (2013.01); *A63B 2220/52* (2013.01); *A63B 2220/56* (2013.01); *A63B 2220/805* (2013.01); *A63B 2220/806* (2013.01); *A63B 2220/808* (2013.01); *A63B 2220/833* (2013.01); *A63B 2220/836* (2013.01); *A63B 2225/02* (2013.01); *A63B 2225/15* (2013.01); *A63B 2225/20* (2013.01); *A63B 2225/50* (2013.01); *A63B 2225/54* (2013.01); *A63B 2230/01* (2013.01); *A63B 2230/06* (2013.01); *A63B 2230/60* (2013.01)

(58) Field of Classification Search
CPC ............ A61B 2562/0219; A61B 5/486; A61B 2505/09; G06F 19/3481; A61N 1/36003; A61N 1/00; A63B 22/0605; A63B 2220/806; A63B 71/0622; A63B 22/0235; A63B 22/02; A63B 2220/13; A63B 2220/808; A63B 2220/805; A63B 2220/56; A63B 2213/004; A63B 2220/833; A63B 2220/836; A63B 22/0664; A63B 22/04; A63B 2225/02; A63B 2230/06; A63B 2225/20; A63B 2225/15; A63B 2220/51; A63B 2071/0655; A63B 2220/52; A63B 2220/40; A63B 2220/30; A63B 2220/18; A63B 2230/60; A63B 2071/065; A63B 2071/0625; A63B 22/0242; A63B 2230/01; A63B 69/0028; A63B 2225/50; A63B 2225/54; A63B 2220/36; G09B 19/0038

See application file for complete search history.

(56) References Cited

U.S. PATENT DOCUMENTS

| | | |
|---|---|---|
| 44,198 A | 9/1864 | Jones |
| 54,530 A | 5/1866 | Hadfield |
| 60,883 A | 1/1867 | Hadfield |
| 68,637 A | 9/1867 | Mason |
| 72,631 A | 12/1867 | Hadfield |
| 76,053 A | 3/1868 | Colwell |
| 100,867 A | 3/1870 | Curran |
| 217,918 A | 7/1879 | White |
| 219,439 A | 9/1879 | Blend |
| 458,136 A | 8/1891 | Wilder |
| 823,812 A | 6/1906 | Ritter |
| 871,074 A | 11/1907 | Stockton |
| 1,193,374 A | 8/1916 | Gilliam |
| 1,223,707 A | 4/1917 | Lyon |
| 1,336,774 A | 4/1920 | Cooper |
| 1,504,166 A | 8/1924 | Thornley |
| 1,507,554 A | 9/1924 | Cooper |
| 1,553,520 A | 9/1925 | Dougherty |
| 1,578,852 A | 3/1926 | Schmutzer |
| 1,580,508 A | 4/1926 | Liles |
| 1,586,254 A | 5/1926 | Lovejoy |
| 2,050,500 A | 8/1936 | Osborn |
| 2,108,566 A | 2/1938 | Brooke |
| 2,109,188 A | 2/1938 | Elizaveta |
| 2,327,671 A | 8/1943 | Rupprecht |
| 2,438,979 A | 4/1948 | Lea |
| 2,719,568 A | 10/1955 | Webb |
| 2,785,004 A | 3/1957 | Cooper |
| 2,819,755 A | 1/1958 | Harold et al. |
| 2,871,915 A | 2/1959 | Hogan |
| 2,892,455 A | 6/1959 | Hutton |
| 2,991,523 A | 7/1961 | Del Conte |
| 3,085,357 A | 4/1963 | Nissen et al. |
| 3,140,869 A | 7/1964 | Pacuk |
| 3,165,314 A | 1/1965 | Clearman et al. |
| 3,176,793 A | 4/1965 | Roland |
| 3,252,704 A | 5/1966 | Louise |
| 3,332,176 A | 7/1967 | Knetzer |
| 3,335,529 A | 8/1967 | Gedney |
| 3,353,309 A | 11/1967 | Kwake |
| 3,428,015 A | 2/1969 | Cloud |
| 3,730,587 A | 5/1973 | Bloxham et al. |
| 3,738,027 A | 6/1973 | Schoch |
| 3,747,596 A | 7/1973 | Mills |
| 3,768,467 A | 10/1973 | Jennings |
| 3,778,052 A | 12/1973 | Andow et al. |
| 3,824,994 A | 7/1974 | Soderberg, Sr. |
| 3,911,913 A | 10/1975 | June |
| 4,149,712 A | 4/1979 | Murphy |
| 4,188,966 A | 2/1980 | Palmer et al. |
| 4,205,839 A | 6/1980 | Best |
| 4,211,426 A | 7/1980 | Motloch |
| 4,257,407 A | 3/1981 | Macchi |
| 4,343,302 A | 8/1982 | Dillon |
| 4,411,422 A | 10/1983 | Solloway |
| 4,479,646 A | 10/1984 | Beistegui Chirapozu |
| 4,509,513 A | 4/1985 | Lasley |
| 4,536,163 A | 8/1985 | Schnirch et al. |
| 4,551,108 A | 11/1985 | Bass |
| 4,576,376 A | 3/1986 | Miller |
| 4,621,621 A | 11/1986 | Marsalis |
| 4,655,447 A | 4/1987 | Dubrinsky et al. |
| 4,712,788 A | 12/1987 | Gaudreau, Jr. |
| 4,731,882 A | 3/1988 | Ekman |
| 4,776,581 A | 10/1988 | Shepherdson |
| 4,805,601 A | 2/1989 | Eischen, Sr. |
| 4,861,021 A | 8/1989 | Edwards et al. |
| 4,863,163 A | 9/1989 | Wehrell |
| 4,887,317 A | 12/1989 | Phillips et al. |
| 4,911,426 A | 3/1990 | Scales |
| 4,921,245 A | 5/1990 | Roberts |
| 4,922,426 A | 5/1990 | Obara et al. |
| 4,934,694 A | 6/1990 | McIntosh |
| 4,941,497 A | 7/1990 | Prather et al. |
| 4,959,047 A | 9/1990 | Tripp, Jr. |
| 4,961,544 A | 10/1990 | Bidoia |
| 4,961,573 A | 10/1990 | Wehrell |
| 4,968,028 A | 11/1990 | Wehrell |
| 4,974,829 A | 12/1990 | Gamow et al. |
| 4,976,623 A | 12/1990 | Owsley |
| 5,000,440 A | 3/1991 | Lynch |
| 5,029,579 A | 7/1991 | Trammel |
| 5,048,836 A | 9/1991 | Bellagamba |

(56) References Cited

U.S. PATENT DOCUMENTS

| | | |
|---|---|---|
| 5,064,193 A | 11/1991 | Sainte et al. |
| 5,070,816 A | 12/1991 | Wehrell |
| 5,075,902 A | 12/1991 | McReynolds et al. |
| 5,133,339 A | 7/1992 | Whalen et al. |
| 5,156,549 A | 10/1992 | Wehrell |
| 5,174,590 A | 12/1992 | Kerley et al. |
| 5,176,597 A | 1/1993 | Bryne |
| 5,221,241 A | 6/1993 | Bare |
| 5,242,339 A | 9/1993 | Thornton |
| 5,273,502 A | 12/1993 | Kelsey et al. |
| 5,275,426 A | 1/1994 | Tankersley |
| 5,288,283 A | 2/1994 | Meeker |
| 5,295,929 A | 3/1994 | Weisz |
| 5,348,035 A | 9/1994 | Porter |
| 5,356,361 A | 10/1994 | Watenpaugh |
| 5,360,384 A | 11/1994 | Toensing |
| 5,362,298 A | 11/1994 | Brown et al. |
| 5,368,532 A | 11/1994 | Farnet |
| 5,368,533 A | 11/1994 | Feuer et al. |
| 5,372,561 A | 12/1994 | Lynch |
| 5,391,115 A | 2/1995 | Bessey |
| 5,398,678 A | 3/1995 | Gamow |
| 5,403,253 A | 4/1995 | Gaylord |
| 5,403,270 A | 4/1995 | Schipper |
| 5,435,798 A | 7/1995 | Habing et al. |
| 5,512,029 A | 4/1996 | Barnard et al. |
| 5,526,893 A | 6/1996 | Higer |
| 5,527,242 A | 6/1996 | Gangloff |
| 5,569,129 A | 10/1996 | Seif Naraghi et al. |
| 5,571,062 A | 11/1996 | Saganovsky |
| 5,577,984 A | 11/1996 | Bare, II |
| 5,593,368 A | 1/1997 | Checketts |
| 5,601,527 A | 2/1997 | Selkowitz |
| 5,603,677 A | 2/1997 | Sollo |
| 5,623,944 A | 4/1997 | Nashner |
| 5,626,540 A | 5/1997 | Hall |
| 5,662,311 A | 9/1997 | Waedekin et al. |
| 5,662,560 A | 9/1997 | Svendsen et al. |
| 5,667,461 A | 9/1997 | Hall |
| 5,671,822 A | 9/1997 | Phillips |
| 5,695,432 A | 12/1997 | Soderlund |
| 5,702,323 A | 12/1997 | Poulton |
| 5,704,880 A | 1/1998 | Amatulle |
| 5,704,881 A | 1/1998 | Dudley |
| 5,706,822 A | 1/1998 | Khavari |
| 5,738,612 A | 4/1998 | Tsuda |
| 5,738,616 A | 4/1998 | Robertson |
| 5,788,606 A | 8/1998 | Rich |
| 5,799,652 A | 9/1998 | Kotliar |
| 5,816,983 A | 10/1998 | Dawes et al. |
| 5,830,162 A | 11/1998 | Giovannetti |
| 5,857,944 A | 1/1999 | Cone et al. |
| 5,860,857 A | 1/1999 | Wasastjerna et al. |
| 5,876,311 A | 3/1999 | Coates et al. |
| 5,893,387 A | 4/1999 | Dubats et al. |
| 5,919,119 A | 7/1999 | Bohmer et al. |
| 5,919,419 A | 7/1999 | Majuri |
| 5,921,892 A | 7/1999 | Easton |
| 5,960,480 A | 10/1999 | Neustater et al. |
| 6,027,464 A | 2/2000 | Dahlquist |
| 6,033,344 A | 3/2000 | Trulaske et al. |
| 6,042,537 A | 3/2000 | Kaiser |
| 6,093,024 A | 7/2000 | Sokolowski |
| 6,120,418 A | 9/2000 | Plough |
| 6,128,782 A | 10/2000 | Young et al. |
| 6,146,315 A | 11/2000 | Schonenberger |
| 6,158,389 A | 12/2000 | Wehrell |
| 6,162,151 A | 12/2000 | Tani et al. |
| 6,174,268 B1 | 1/2001 | Novak |
| 6,217,493 B1 | 4/2001 | Spletzer |
| 6,223,854 B1 | 5/2001 | Nolz |
| 6,244,379 B1 | 6/2001 | Larson |
| 6,261,205 B1 | 7/2001 | Elefson |
| 6,270,414 B2 | 8/2001 | Roelofs |
| 6,273,844 B1 | 8/2001 | Kelsey et al. |
| 6,280,361 B1 | 8/2001 | Harvey et al. |
| 6,332,290 B1 | 12/2001 | DeLamare |
| 6,332,354 B1 | 12/2001 | Lalor et al. |
| 6,405,685 B1 | 6/2002 | Cox |
| 6,436,009 B1 | 8/2002 | Marucci |
| 6,438,756 B1 | 8/2002 | Colorado |
| 6,482,128 B1 | 11/2002 | Michalow |
| 6,490,733 B1 | 12/2002 | Casaubon |
| 6,494,811 B1 | 12/2002 | Alessandri |
| 6,527,285 B1 | 3/2003 | Calandro, II |
| 6,527,678 B1 | 3/2003 | Wang et al. |
| 6,539,946 B2 | 4/2003 | Weyergans |
| 6,554,747 B1 | 4/2003 | Rempe |
| 6,565,624 B2 | 5/2003 | Kutt et al. |
| 6,578,594 B1 | 6/2003 | Bowen et al. |
| 6,609,054 B2 | 8/2003 | Wallace |
| 6,612,845 B1 | 9/2003 | Macri et al. |
| 6,645,126 B1 | 11/2003 | Martin et al. |
| 6,648,411 B2 | 11/2003 | Julien |
| 6,656,091 B1 | 12/2003 | Abelbeck et al. |
| 6,666,801 B1 | 12/2003 | Michalow |
| 6,666,831 B1 | 12/2003 | Edgerton et al. |
| 6,669,605 B2 | 12/2003 | Scates |
| 6,679,510 B2 | 1/2004 | Perena |
| 6,689,075 B2 | 2/2004 | West |
| 6,742,523 B2 | 6/2004 | Dubats |
| D495,384 S | 8/2004 | Rolfes |
| 6,783,482 B2 | 8/2004 | Oglesby et al. |
| 6,821,233 B1 | 11/2004 | Colombo et al. |
| 6,892,403 B2 | 5/2005 | Liljedahl |
| 6,905,459 B2 | 6/2005 | Humphries, Jr. |
| 6,918,858 B2 | 7/2005 | Watterson et al. |
| 6,932,709 B1 | 8/2005 | Gubitosi et al. |
| 6,935,353 B2 | 8/2005 | Hawkes |
| 6,966,870 B2 | 11/2005 | Lan |
| 6,978,497 B1 | 12/2005 | Takizawa |
| 6,988,951 B1 | 1/2006 | Newman et al. |
| 7,141,007 B2 | 11/2006 | Egger |
| 7,166,064 B2 | 1/2007 | Watterson et al. |
| 7,240,621 B2 | 7/2007 | Chepurny et al. |
| 7,278,958 B2 | 10/2007 | Morgan |
| 7,294,094 B1 | 11/2007 | Howle |
| 7,341,543 B2 | 3/2008 | Dandy |
| 7,381,163 B2 | 6/2008 | Gordon et al. |
| 7,472,964 B2 | 1/2009 | King |
| 7,494,453 B2 | 2/2009 | Wehrell |
| 7,544,172 B2 | 6/2009 | Santos-Munne et al. |
| 7,556,040 B2 | 7/2009 | Meyer et al. |
| 7,572,190 B2 | 8/2009 | Habing |
| 7,572,209 B2 | 8/2009 | Brennan |
| 7,591,795 B2 | 9/2009 | Whalen et al. |
| 7,594,281 B1 | 9/2009 | Stinson et al. |
| 7,608,025 B1 | 10/2009 | Best |
| 7,614,991 B2 | 11/2009 | Fox |
| 7,625,320 B2 | 12/2009 | Wehrell |
| 7,651,450 B2 | 1/2010 | Wehrell |
| 7,666,126 B2 | 2/2010 | Rempe |
| 7,727,076 B2 | 6/2010 | Bapst et al. |
| 7,780,587 B2 | 8/2010 | Thornton et al. |
| 7,785,242 B2 | 8/2010 | Solomon |
| 7,837,597 B2 | 11/2010 | Reyes et al. |
| 7,850,629 B2 | 12/2010 | Ravikumar |
| 7,857,731 B2 | 12/2010 | Hickman et al. |
| 7,862,478 B2 | 1/2011 | Watterson et al. |
| 7,874,223 B2 | 1/2011 | Sugar et al. |
| 7,883,450 B2 | 2/2011 | Hidler |
| 7,887,471 B2 | 2/2011 | McSorley |
| 7,914,420 B2 | 3/2011 | Daly et al. |
| 7,938,756 B2 | 5/2011 | Rodetsky et al. |
| 7,955,219 B2 | 6/2011 | Birrell et al. |
| 7,998,040 B2 | 8/2011 | Kram et al. |
| 8,083,643 B2 | 12/2011 | Ng et al. |
| 8,109,478 B2 | 2/2012 | Tristao |
| 8,152,699 B1 | 4/2012 | Ma et al. |
| 8,172,724 B2 | 5/2012 | Solomon |
| 8,221,293 B2 | 7/2012 | Hoffman et al. |
| 8,235,724 B2 | 8/2012 | Gilley et al. |
| 8,246,354 B2 | 8/2012 | Chu et al. |
| 8,251,863 B2 | 8/2012 | Faulring et al. |

(56) References Cited

U.S. PATENT DOCUMENTS

| | | |
|---|---|---|
| 8,425,620 B2 | 4/2013 | Johnson et al. |
| 8,447,401 B2 | 5/2013 | Miesel et al. |
| 8,464,716 B2 | 6/2013 | Kuehne et al. |
| 8,470,051 B2 | 6/2013 | Moyer et al. |
| 8,480,602 B1 | 7/2013 | Cook |
| 8,656,516 B1 | 2/2014 | Reinhardt Rawlings et al. |
| 8,762,167 B2 | 6/2014 | Blander et al. |
| 8,840,572 B2 | 9/2014 | Whalen et al. |
| 8,888,664 B1 | 11/2014 | Butler |
| 8,968,163 B1 | 3/2015 | Vidmar |
| 9,087,454 B2 | 7/2015 | Crivello et al. |
| 9,314,393 B2 | 4/2016 | Kim et al. |
| 9,370,680 B1 | 6/2016 | Macaulay et al. |
| 9,474,934 B1 | 10/2016 | Krueger et al. |
| 9,483,957 B1 | 11/2016 | Fuemmeler |
| 9,672,754 B2 | 6/2017 | Yuen et al. |
| 9,713,439 B1 | 7/2017 | Wu et al. |
| 2001/0018564 A1 | 8/2001 | Manor et al. |
| 2002/0010056 A1 | 1/2002 | Borsheim |
| 2002/0022554 A1 | 2/2002 | Borsheim |
| 2002/0032103 A1 | 3/2002 | Cook |
| 2002/0065173 A1 | 5/2002 | Cook |
| 2003/0032904 A1 | 2/2003 | Egger |
| 2003/0204148 A1 | 10/2003 | Lange et al. |
| 2004/0016043 A1 | 1/2004 | Uno et al. |
| 2004/0019304 A1 | 1/2004 | West |
| 2004/0171465 A1 | 9/2004 | Hald et al. |
| 2004/0212240 A1 | 10/2004 | Zwezdaryk |
| 2004/0238285 A1 | 12/2004 | Stokes |
| 2004/0245298 A1 | 12/2004 | Refsum |
| 2004/0249675 A1 | 12/2004 | Stark et al. |
| 2005/0026757 A1 | 2/2005 | Creary |
| 2005/0075680 A1 | 4/2005 | Lowry et al. |
| 2005/0101448 A1 | 5/2005 | He et al. |
| 2005/0183759 A1 | 8/2005 | Wolfe |
| 2005/0250624 A1 | 11/2005 | Yu |
| 2006/0009333 A1 | 1/2006 | Wang |
| 2006/0031984 A1 | 2/2006 | Takizawa |
| 2006/0052728 A1 | 3/2006 | Kerrigan et al. |
| 2006/0062413 A1 | 3/2006 | Wehrell |
| 2006/0079378 A1 | 4/2006 | Ader |
| 2006/0185065 A1 | 8/2006 | Allen |
| 2006/0190051 A1 | 8/2006 | Gerber et al. |
| 2006/0199712 A1 | 9/2006 | Barnard et al. |
| 2006/0240956 A1 | 10/2006 | Piane |
| 2007/0016116 A1 | 1/2007 | Reinkensmeyer et al. |
| 2007/0054783 A1 | 3/2007 | Egger |
| 2007/0219059 A1 | 9/2007 | Schwartz et al. |
| 2007/0219069 A1 | 9/2007 | Nativ |
| 2007/0272484 A1 | 11/2007 | Helms |
| 2008/0017227 A1 | 1/2008 | Ward |
| 2008/0070757 A1 | 3/2008 | Albert |
| 2008/0229495 A1 | 9/2008 | Takizawa |
| 2008/0246581 A1 | 10/2008 | Irie et al. |
| 2008/0281633 A1 | 11/2008 | Burdea et al. |
| 2008/0282442 A1 | 11/2008 | Bauvois |
| 2008/0300118 A1 | 12/2008 | Wehrell |
| 2008/0306412 A1 | 12/2008 | Nieminen et al. |
| 2009/0014004 A1 | 1/2009 | Whalen et al. |
| 2009/0036272 A1 | 2/2009 | Yoo |
| 2009/0047644 A1 | 2/2009 | Mensah et al. |
| 2009/0082700 A1 | 3/2009 | Whalen et al. |
| 2009/0221404 A1 | 9/2009 | Dorogusker et al. |
| 2009/0236176 A1 | 9/2009 | Sheu et al. |
| 2009/0255531 A1 | 10/2009 | Johnson et al. |
| 2009/0269728 A1 | 10/2009 | Verstegen et al. |
| 2010/0000547 A1 | 1/2010 | Johnson et al. |
| 2010/0006737 A1 | 1/2010 | Colombo et al. |
| 2010/0139057 A1 | 6/2010 | Soderberg et al. |
| 2010/0170546 A1 | 7/2010 | Popovic et al. |
| 2010/0197462 A1 | 8/2010 | Piane |
| 2010/0197465 A1 | 8/2010 | Stevenson |
| 2010/0248903 A1 | 9/2010 | Cardile |
| 2010/0279837 A1 | 11/2010 | Stengel |
| 2010/0298102 A1 | 11/2010 | Bosecker et al. |
| 2011/0071442 A1 | 3/2011 | Park et al. |
| 2011/0086743 A1 | 4/2011 | Stewart |
| 2011/0098157 A1 | 4/2011 | Whalen et al. |
| 2011/0098615 A1 | 4/2011 | Whalen et al. |
| 2011/0179068 A1 | 7/2011 | O'Brien |
| 2011/0219899 A1 | 9/2011 | Dize et al. |
| 2012/0004581 A1 | 1/2012 | Dinon |
| 2012/0029666 A1 | 2/2012 | Crowley et al. |
| 2012/0042917 A1 | 2/2012 | Workman et al. |
| 2012/0238921 A1 | 9/2012 | Kuehne et al. |
| 2012/0277643 A1 | 11/2012 | Whalen et al. |
| 2012/0302301 A1 | 11/2012 | Homsi |
| 2013/0095459 A1 | 4/2013 | Tran |
| 2013/0324893 A1 | 12/2013 | Kuehne et al. |
| 2013/0325491 A1 | 12/2013 | Ferrari |
| 2014/0026893 A1 | 1/2014 | Johnson et al. |
| 2014/0081661 A1 | 3/2014 | Fu et al. |
| 2014/0113775 A1 | 4/2014 | Egan |
| 2014/0147820 A1 | 5/2014 | Snow et al. |
| 2014/0228985 A1 | 8/2014 | Elliott et al. |
| 2015/0011917 A1 | 1/2015 | Whalen et al. |
| 2015/0199494 A1 | 7/2015 | Koduri et al. |
| 2015/0251055 A1 | 9/2015 | Ashby |
| 2015/0379239 A1 | 12/2015 | Basta et al. |
| 2016/0000155 A1 | 1/2016 | Marecek et al. |
| 2016/0001118 A1 | 1/2016 | Kuehne et al. |
| 2016/0001119 A1 | 1/2016 | Jue et al. |
| 2016/0008650 A1 | 1/2016 | Jue et al. |
| 2016/0073704 A1 | 3/2016 | Basta et al. |

FOREIGN PATENT DOCUMENTS

| | | |
|---|---|---|
| CN | 2208414 Y | 9/1995 |
| CN | 202860021 | 4/2013 |
| DE | 02623091 A1 | 11/1977 |
| DE | 29508818 U1 | 11/1995 |
| DE | 19502801 C2 | 10/1996 |
| DE | 20004959 U1 | 6/2000 |
| DE | 20305670 U1 | 8/2003 |
| DE | 20313772 U1 | 12/2003 |
| DE | 10362043 A1 | 5/2005 |
| DE | 102006010887 A1 | 9/2007 |
| EP | 0917890 A2 | 5/1999 |
| EP | 2512758 A2 | 10/2012 |
| EP | 2532927 A2 | 12/2012 |
| ES | 2151390 A1 | 12/2000 |
| FR | 1180387 A1 | 6/1959 |
| FR | 2755865 A1 | 5/1998 |
| FR | 2831065 A1 | 4/2003 |
| FR | 2846888 A1 | 5/2004 |
| FR | 2939050 A1 | 6/2010 |
| GB | 2128488 A | 5/1984 |
| GB | 2314512 A | 1/1998 |
| JP | 59-002993 | 1/1984 |
| JP | 63109878 A | 5/1988 |
| JP | 05-500760 | 2/1993 |
| JP | 05-049596 A | 6/1993 |
| JP | 1022334 | 10/1998 |
| JP | 11-113988 A | 4/1999 |
| JP | 2000-342713 | 12/2000 |
| JP | 2001-112886 | 4/2001 |
| JP | 2001-517187 A | 10/2001 |
| JP | 2002-28202 A | 1/2002 |
| JP | 2002-360644 | 12/2002 |
| JP | 2004-073445 A | 3/2004 |
| JP | 2004329365 A | 11/2004 |
| JP | 2004353439 A | 12/2004 |
| JP | 2005-102798 A | 4/2005 |
| JP | 2007-151676 A | 6/2007 |
| JP | 2008-538511 A | 10/2008 |
| JP | 1395000 | 8/2010 |
| JP | 1421980 | 8/2011 |
| JP | 2012-214936 A | 11/2012 |
| KR | 20030086404 | 11/2003 |
| TW | 425592 B | 3/2001 |
| TW | I235427 B | 7/2005 |
| TW | M339250 U | 9/2008 |
| WO | WO96/31256 A1 | 10/1996 |
| WO | WO99/30271 A1 | 6/1999 |

(56) References Cited

FOREIGN PATENT DOCUMENTS

| WO | WO01/24900 | A1 | 4/2001 |
|---|---|---|---|
| WO | WO02/098516 | A1 | 12/2002 |
| WO | WO2004/080365 | A1 | 9/2004 |
| WO | WO2004/103176 | A1 | 12/2004 |
| WO | WO2006/050787 | A1 | 5/2006 |
| WO | WO2006/061834 | A2 | 6/2006 |
| WO | WO2007/038888 | A1 | 4/2007 |
| WO | WO2007/115565 | A2 | 10/2007 |
| WO | WO2008/030366 | A2 | 3/2008 |
| WO | WO2008/058567 | A1 | 5/2008 |
| WO | WO2009/151630 | A1 | 12/2009 |
| WO | WO2011/089632 | A1 | 7/2011 |
| WO | WO2011/112898 | A1 | 9/2011 |
| WO | WO2012/107700 | A2 | 8/2012 |
| WO | WO2012/118143 | A1 | 9/2012 |
| WO | WO2013/019956 | A1 | 2/2013 |
| WO | WO2013/021709 | A1 | 2/2013 |
| WO | WO2014/138228 | A1 | 9/2014 |
| WO | WO2015/195983 | A1 | 12/2015 |

OTHER PUBLICATIONS

"Feedback Control System;" The Encyclopedia Americana International Edition; pp. 82-84; Dec. 2003.

Burgess et al.; Overground walking speed changes when subjected to body weight support conditions for nonimpaired and post stroke individuals; J NeuroEng Rehabil.; 7(6); 10 pgs.; Feb. 2010.

Capó-Lugo et al.; Maximum walking speeds obtained using treadmill and overground robot system in persons with post-stroke hemiplegia; J NeuroEng Rehabil.; 9(80); 14 pgs.; Oct. 2012.

Díaz et al.; Lower-Limb Robotic Rehabilitation: Literature Review and Challenges; Hindawi Pub. Corp.; Journal of Robotics; vol. 2011; Art. ID 759764; 11 pgs.; (accepted for publn.) Sep. 2011.

Hamilton; Low-Tech Alternative to AlterG on Market; Runner's World; 2 pgs.; Aug. 16, 2012; (printed from internet: http://www.runnersworld.com/elite-runners/low-tech-alternative-alterg-market).

Hargens et al.; Lower body negative pressure to provide load bearing in space; Aviat Space Environ Med; 62(10); pp. 934-937; Oct. 1991.

Kawai et al.; Rehabilitation apparatus for treadmill walking using lower body positive pressue (Japanese & English abstracts); Aerospace and Environmental Medicine; vol. 44; No. 4; (year of pub. sufficiently earlier than effective US filing date and any foreign priority date) 2007.

Lillegard, R.; Running on air (retrieved Aug. 10, 2016 from the internet: http://www.lightspeedrunningandrehabilitation.com/in-the-news/running-on-air/#more-89); Duluth Superior Magazine; 3 pgs.; Jul. 2, 2012.

Pates, K.; Duluth physical therapist develops running aid; (retrieved Aug. 10, 2016 from the internet: http://www.lightspeedrunningandrehabilitation.com/in-the-news/duluth-physical-therapist-develops-running-aid/#more-92); Duluth News Tribune; 3 pgs.; Jul. 25, 2012.

Patton et al.; KineAssist: Design and development of a robotic overground gait and balance therapy device; Top Stroke Rebabil.; 15(2); pp. 131-139; Mar.-Apr. 2008.

Vacu Well Wellness & Beauty; Company History and Vacu Well Power Professional treadmill specifications; printed from website (http://www.vacuwell.com); 3 pgs.; printed Apr. 4, 2012.

Whalen et al.; Design U.S. Appl. No. 29/337,097 entitled "Adjustable Positive Pressure Support System," filed May 14, 2009.

Whalen et al.; U.S. Appl. No. 15/046,358 entitled "System, method and apparatus for applying air pressure on a portion of the body of an individual," filed Feb. 17, 2016.

Whalen et al.; U.S. Appl. No. 15/143,351 entitled "Systems, methods and apparatus for differential air pressure devices," filed Apr. 29, 2016.

Long et al.; U.S. Appl. No. 15/319,629 entitled "Pressure chamber and lift for differential air pressure system with medical data collection capabilities," filed Dec. 16, 2016.

Kuehne et al.; U.S. Appl. No. 15/588,549 entitled "Differential air pressure systems," filed May 5, 2017.

Kuehne et al.*, U.S. Appl. No. 15/916,083 entitled "Monocolumn unweighting systems," filed Mar. 8, 2018.

Whalen et al.; U.S. Appl. No. 15/963,960 entitled "Systems, methods and apparatus for differential air pressure devices," filed Apr. 26, 2018.

Kuehne et al.; U.S. Appl. No. 15/993,136 entitled "Differential air pressure systems and methods of using and calibrating such systems for mobility impaired users," filed May 30, 2018.

Basta et al.; U.S. Appl. No. 16/010,149 entitled "Unweighting garments for simultaneous use with unweighting andd fall safety systems," filed Jun. 15, 2018.

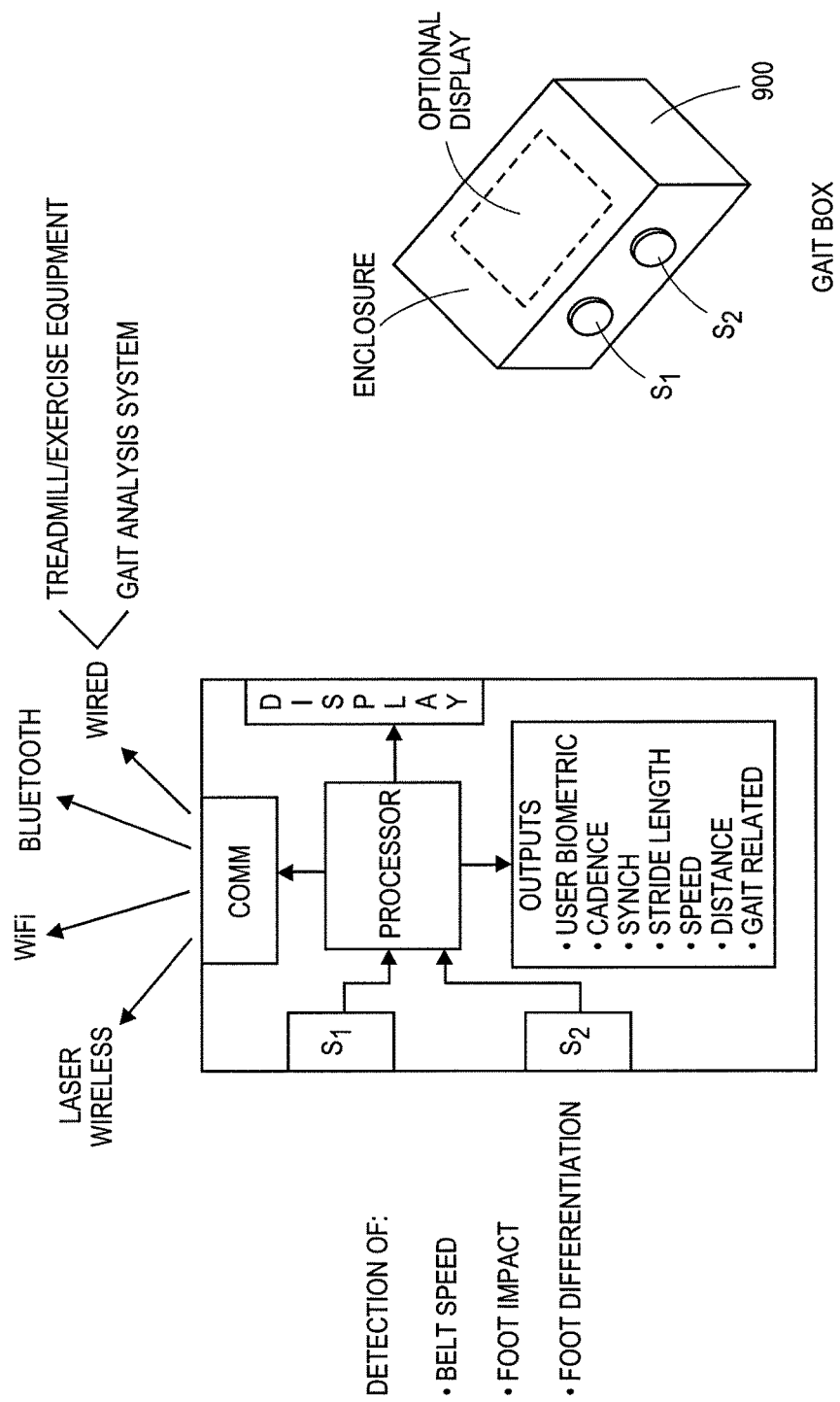

Symmetrical Stride

Stride Phase Asymmetry

Stride Jitter

METHOD OF GAIT EVALUATION AND TRAINING WITH DIFFERENTIAL PRESSURE SYSTEM

CROSS REFERENCE TO RELATED APPLICATIONS

This application claims priority to U.S. Provisional Patent Application No. 61/785,317, filed Mar. 14, 2013 which is herein incorporated by reference in its entirety.

This application may be related to any of the following patent applications, each of which is herein incorporated by reference in its entirety: U.S. Provisional Patent Application No. 61/651,415, filed on May 24, 2012, U.S. Pat. No. 7,591,795 issued on Sep. 22, 2009, U.S. application Ser. No. 12/236,459 filed on Sep. 23, 2008, U.S. application Ser. No. 12/236,465 filed on Sep. 23, 2008, U.S. application Ser. No. 12/236,468 filed on Sep. 23, 2008, International Application No. PCT/US2006/038591 filed on Sep. 28, 2006, U.S. Provisional Application No. 60/999,102 filed on Oct. 15, 2007, U.S. Provisional Application No. 60/999,101 filed on Oct. 15, 2007, U.S. Provisional Application No. 60/999,061 filed on Oct. 15, 2007, U.S. Provisional Application No. 60/999,060 filed on Oct. 15, 2007, U.S. application Ser. No. 12/761,316 filed on Apr. 15, 2010, U.S. application Ser. No. 12/761,312 filed on Apr. 15, 2010, International Application No. PCT/US2008/011832 filed on Oct. 15, 2008, International Application No. PCT/US2008/011807 filed on Oct. 15, 2008, U.S. Provisional Application No. 61/178,901 filed on May 15, 2009, U.S. application Ser. No. 12/778,747 filed on May 12, 2010, International Application No. PCT/US2010/034518 filed on May 12, 2010, U.S. Design application Ser. No. 29/337,097 filed on May 14, 2009, U.S. Provisional Application No. 61/454,432 filed on Mar. 18, 2011, U.S. application Ser. No. 13/423,124 filed on Mar. 16, 2012, International Application No. PCT/US2012/029554 filed on Mar. 16, 2012 and U.S. Pat. No. 5,133,339 issued on Jul. 28, 1992.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates to biomechanical evaluation and training systems, especially those for correction or improvement of gait and especially in conjunction with an assistance system such as a differential air pressure assistance system.

BACKGROUND

Gait correction is a key goal of therapists in healing and training their patients. Gait training helps injured patients to recover from injuries that affect how they run, walk, and jog and helps prevent future injuries. Even though methods of quantitative measuring gait are well known, there are significant limitations in current methods. Many gait evaluation tools are designed primarily to measure gait function at full body weight, and many patients are unable to bear full body weight or have abnormal gait at full body weight and lack the ability to effectively alter their gait under such load. Additionally, these systems are typically designed for investigational purposes, presenting detailed data to analysis-oriented researchers. Unloading systems such as harnesses or pools apply pressure in a fashion that alters gait undesirably and therefore impair accurate evaluation or training of gait. Due to the way differential air pressure unweighing systems support their patients, they do not introduce the same external factors that harnesses and pools do. Because of the lack of gait measurement tools in differential air pressure systems, many clinical therapists, who are tasked with correcting gait and not only measuring it, often rely exclusively on their experience to estimate what and how the patient should be training with respect to their gait. This approach has shown to be effective, however the practice is more art than science, so standard of care can vary between therapists providing treatment.

Though a number of gait measurement tools exist primarily for laboratory environments, there are several reasons why these systems are not widely used in the rehab environment. In the lab environment, the tools to instrument a patient are generally more costly than most therapy centers can afford. The laboratories themselves are designed to gather data, not to effectively treat patient problems. Even an analysis done on the data that has been gathered is rarely helpful to the patient during the treatment session, partially because the labs do not have quantitative data available in real time. Often the data is also not presented in an understandable way so laboratory environments are sub-optimal at treating patients.

In addition to the limitations of the current equipment used for gait measurement, many patients simply lack the strength or experience too much pain to perform suitably in full weightbearing systems to attain gait improvements. As a result of the variations in patient training ability as well as the variety of gait systems, there remains a need for improved systems to train and improve gait in patients.

SUMMARY OF THE DISCLOSURE

In general, in one embodiment, an integrated unweighted gait training system, includes an unweighting system comprising a computer controller, a gait measurement system in communication with the controller, and a display in communication with the computer controller adapted and configured to provide real-time feedback to a user of the integrated unweighting gait training system.

This and other embodiments can include one or more of the following features. In one aspect, the unweighting system can be a differential air pressure unweighting system. In another aspect, the unweighting system can be a non-DAP unweighting system. In a further aspect, the non-DAP unweighting system can be a support frame type non-DAP unweighting system. In an alternative aspect, the non-DAP unweighting system can be a curved arch type non-DAP unweighting system. In yet another aspect, the non-DAP unweighting system can be an unweighting arch type non-DAP unweighting system. In still another aspect, the non-DAP unweighting system can be a monocolumn type non-DAP unweighing system. In one aspect, the non-DAP unweighting system can be a cantilevered type non-DAP unweighting system. In another aspect, the gait measurement system can further include an enclosure, a pair of sensors supported by the enclosure and positioned such that when the enclosure is coupled to a treadmill of the integrated unweighting system a portion of the tread is within the detectable range of the pair of sensors, and a processor in communication with the pair of sensors and having computer readable instructions to receive and process an output from the pair of sensors and to perform calculations related to obtaining gait parameters based on the input from the sensors. In a further aspect, the processor can perform calculations to obtain tread belt speed, time of foot impact and left/right foot indication.

In general, in one embodiment, a self-contained gait feedback device for detecting motion of a user on a treadmill includes an enclosure, a pair of sensors supported by the enclosure and positioned such that when the housing is coupled to the treadmill a portion of the tread is within the detectable range of the pair of sensors, a processor supported by the enclosure and in communication with the pair of sensors and having computer readable instructions to receive and process an output from the pair of sensors, and a display in communication with the processor supported by the disclosure.

This and other embodiments can include one or more of the following features. In one aspect, the self-contained feedback device can include the computer readable instructions to receive and process an output from the sensors and can further include performing calculations related to obtaining one of more gait parameters based in part on the output from the pair of sensors. In another aspect, the self-contained feedback device can include the computer readable instructions to receive and process an output from the sensors and can further include outputting the one of more gait parameters to the display. In a further aspect, the self-contained feedback device can include the display and can further include a processor having computer readable instructions for receiving and performing calculations related to obtaining one of more gait parameters based in part on the output from the pair of sensors. In an alternative aspect, the self-contained feedback device can include the computer readable instructions of the processor in the display and can further include outputting the one of more gait parameters on the display. In yet another aspect, the processor can be adapted and configured to provide clock signal synchronized sensor output data from the pair of sensors. In still another aspect, the processor can be adapted and configured to provide clock signal synchronized sensor output data from the pair of sensors. In one aspect, the sensors can be IR sensors, optical mouse sensors, laser sensors, proximity sensors, or light sensors. In another aspect, the display can be a PC, a tablet or a smart phone. In a further aspect, communication with the display can be wired or wirelessly. In an alternative aspect, the display can be in communication with the processor supported by the enclosure. In yet another aspect, the self-contained feedback device can further include an unweighting system positioned to provide controlled unweighting of a user of the treadmill, the unweighting system can have a computer controller in communication with the processor. In still another aspect, the display can be adapted and configured to provide real-time feedback to a user of the unweighting system. In one aspect, the unweighting system can be a differential air pressure unweighting system. In another aspect, the unweighting system can be a non-DAP unweighting system. In a further aspect, the non-DAP unweighting system can be a support frame type non-DAP unweighting system. In an alternative aspect, the non-DAP unweighting system can be a curved arch type non-DAP unweighting system. In yet another aspect, the non-DAP unweighting system can be an unweighting arch type non-DAP unweighting system. In still another aspect, the non-DAP unweighting system can be a monocolumn type non-DAP unweighing system. In still another aspect, the non-DAP unweighting system can be a cantilevered type non-DAP unweighting system.

In general, in one embodiment, an integrated differential air pressure assisted gait training system includes a differential air pressure system having a computer controller, at least one gait measurement or indication system in communication with the computer controller, and a computer readable database stored within or accessible to the computer controller comprising collected DAP system data from the differential air pressure system and gait system data from the at least one gait measurement or indication system This and other embodiments can include one or more of the following features. In one aspect, the DAP system data can include one or more of pressure setting and control, calibration data, system type, auxiliary systems, exercise system controls. In another aspect, the gait system data can include video, user worn sensor or equipment sensor. In a further aspect, the computer readable database can further include synthesized data from at least one of DAP system data or gait system data. In an alternative aspect, the synthesized data can be triggered from another data stream. In still another aspect, the synthesized data can be processed data by manipulating one or more data streams. In one aspect, the synthesized data can be calculated data by comparing or relating two or more data streams. In another aspect, the synthesized data can include using algorithms to produce outcomes of one or more data streams. In a further aspect, can further include a display in communication with the computer controller adapted and can be configured to provide real-time feedback to a user of the differential air pressure system. In an alternative aspect, the system can further include video input in database. In yet another aspect, the video data stored can be collected based on a trigger from another component or device of the integrated system. In still another aspect, the database can be accessible to computer controller or accessible to the controller via wired or wireless communication. In one aspect, the system can include at least one gait measurement or indication system and can further include an enclosure, a pair of sensors supported by the enclosure and positioned such that when the enclosure is coupled to a treadmill of the integrated unweighting system a portion of the tread can be within the detectable range of the pair of sensors, and a processor supported by the enclosure and in communication with the pair of sensors and having computer readable instructions to receive and process an output from the pair of sensors and to perform calculations related to obtaining gait parameters based on the input from the sensors.

In general, in one embodiment, a method of training an individual to improve or alter walking or running mechanics by unweighting includes preparing the individual for training in a differential air pressure environment provided by a differential air pressure system, performing a training routine with the individual to improve or alter walking or running mechanics while the user is experiencing unweighting by the differential air pressure system, simultaneously measuring one or more of a user gait parameter or a user biomechanical parameter during the performing step, and collecting the one or more measured user gait parameter or measured user biomechanical parameter under instructions from a controller of the differential air pressure system.

In general, in one embodiment, a method of training an individual to improve or alter walking or running mechanics by unweighting includes preparing the individual for training in a non-differential air pressure environment provided by a non-differential air pressure system, performing a training routine with the individual to improve or alter walking or running mechanics while the user is experiencing unweighting by the non-differential air pressure system, simultaneously measuring one or more of a user gait parameter or a user biomechanical parameter during the performing step, and collecting the one or more measured user gait parameter or measured user biomechanical parameter under instructions from a controller of the non-differential air pressure system.

This and other embodiments can include one or more of the following features. In one aspect, the preparing step can further include the user accessing the differential air pressure environment and initiating the training without assistance. In another aspect, the preparing step can further include the user accessing the differential air pressure environment without assistance and initiating or performing the training with assistance. In a further aspect, the assistance during performing the training can be provided by a person. In an alternative aspect, the assistance during performing the training can be provided automatically by the differential air pressure system. In yet another aspect, the collecting step can further include collecting the individual's heart rate and a treadmill incline measurement. In still another aspect, the collecting step can further include collecting a signal from a heart rate monitor worn by the individual. In one aspect, the collecting step can further include collecting data from a gyroscopic sensor or an accelerometer sensor worn by the patient. In another aspect, the one or more parameters of the user's gait or biomechanics can be one or more of: a stride length, a ground reaction force, a lateral movement of a knee, an angle of a knee, an angle of an ankle, a strike pattern of a forefoot, a strike pattern of a heel, a muscle activation pattern, and a movement symmetry.

In general, in one embodiment, a method of providing integrated differential air pressure assisted gait training includes unweighting the user in an integrated differential air pressure system, performing a therapy routine with the user, collecting under control of the integrated differential air pressure system controller output data from a plurality of components of the integrated differential air pressure system during the unweighting step and the performing step, and recommending a user action for gait correction based on one or more of the output data from the collecting step.

This and other embodiments can include one or more of the following features. In one aspect, the output data can include synthesized data. In another aspect, the collecting step can further include a continuous output data stream, a nearly continuous output data stream, a segmented output data stream, or a synthesized output data stream from the integrated differential air pressure system. In a further aspect, the method can further include storing the output data in a database. In an alternative aspect, the database can contain DAP and gait system data corresponding to a user's progress through a continuum of care. In yet another aspect, the continuum of care can range from immobile, to partially mobile, to fully mobile. In still another aspect, the method can further include comparing the data to data from a device in another segment of the continuum of care. In one aspect, the data from a device from another segment can be gait data collected from a leg worn actuator. In another aspect, the data can be gait data collected from full mobility measurement system. In a further aspect, the recommending step can permit connection of alteration of a parameter of the differential air pressure system or user gait change to real time feedback.

In general, in one embodiment, a self-contained biometric sensor system for detecting motion of a user on a treadmill including an enclosure, a pair of sensors supported by the enclosure and positioned such that when the housing is coupled to a treadmill a portion of the tread is within the detectable range of the pair of sensors, and a processor in communication with the pair of sensors and having computer readable instructions to receive and process an output from the pair of sensors and to perform calculations related to obtaining gait parameters based on the input from the sensors.

This and other embodiments can include one or more of the following features. In one aspect, the processor can be adapted and configured to provide clock signal synchronized sensor output data from the pair of sensors. In another aspect, the sensors can be IR sensors, optical mouse sensors, laser sensors, proximity sensors, or light sensors. In a further aspect, the self-contained biometric sensor system can further include a display in communication with the processor. In an alternative aspect, the display can be a PC, a tablet or a smart phone. In yet another aspect, the display can further include a computer readable code adapted and configured to determine one or more gait parameters based on the processor output. In still another aspect, communication with the display can be wired or wirelessly. In one aspect, the self-contained biometric sensor system can further include an accelerometer attached to the treadmill and configured to provide an output to the processor. In another aspect, the self-contained biometric sensor system can further include an acoustic sensor positioned to detect a footfall sound and configured to provide an output to the processor. In a further aspect, the self-contained biometric sensor system can include the processor computer readable instructions for providing a real-time measurement of a plurality of gait parameters for a user on the treadmill. In an alternative aspect, the plurality of gait parameters of a user on a treadmill can be one or more of speed, cadence, left/right stride length, left/right stride time, foot placement phase asymmetry and stride time jitter.

This and other embodiments can include one or more of the following features. In one aspect, gait measurement or parameters can be provided to the system from a self-contained biometric sensor system that provides accurate, real-time measurement of a plurality of gait parameters of a user on a treadmill within the range of the sensors of the system.

In general, in one embodiment, a system for providing differential air pressure assisted gait training includes a differential air pressure system comprising a computer controller, a gait measurement system in communication with the controller, and a display in communication with the computer controller adapted and configured to provide real-time feedback to a user of the differential air pressure system.

In another aspect, the gait measurement system can be a self-contained biometric sensor system having a computer controller adapted and configured to collect gait data. In a further aspect, there are computer readable instructions in the computer controller of the self-contained biometric sensor system which provides drawing edits on a display. In an alternative aspect, the computer readable instructions in the computer controller which provides for visual indicia on top of a video output. In yet another aspect, the display can be adapted and configured to implement user provided drawings using a touch screen. In one aspect, the display or a touch screen in communication with the system controller can be within reach of the user. In another aspect, the real time feedback to the user of an integrated gait training system can be provided in a representation including a graphic feedback as to the user's gait symmetry. In a further aspect, the real time feedback to the user can be a display of synthesized data. In an alternative aspect, the synthesized data can be triggered from another data stream. In yet another aspect, the synthesized data can be processed data by manipulating one or more data streams. In still another aspect, the synthesized data can be calculated data by comparing or relating two or more data streams. In one aspect, the synthesized data can further include using algorithms to produce outcomes of one or more data streams.

In another aspect, during a user's operation of an integrated gait training system a display output can be changed by a trigger from a sensor or component in a gait measurement system. In a further aspect, the display output can be changed to provide an indication of the user's DAP assisted force asymmetry data. In an alternative aspect, the display output can be changed to provide an indication of the user's DAP cadence asymmetry data. In yet another aspect, the display output can be changed to provide an indication of the user's DAP upper body phase coordination data.

In still another aspect, the display output can be changed. In one aspect, the real time feedback can include an arrow oriented to indicate to the user an indication of a detected force asymmetry. In a further aspect, the real time feedback can include an arrow oriented to indicate to the user an indication of a detected cadence asymmetry. In an alternative aspect, the real time feedback can further include an arrow oriented to indicate to the user an indication of a DAP assisted force asymmetry data.

In yet another aspect, the gait measurement system can further include a camera, a ground force sensor, an inertial sensor on the user's leg, and an inertial sensor on the user's hips. In still another aspect, the gait measurement system can further include an EEMG sensor and an inertial sensor. In one aspect, the gait measurement system can further include a user sensor In another aspect, the user sensor can be on or implanted in a user. In a further aspect, the user sensor can be an instrumented or a marked article worn by the user. In an alternative aspect, the user sensor can be a prosthesis, an exoskeleton, an active EEM, a passive EEM, a biofeedback device, an instrumented or marked pair of shoes, an instrumented or marked pair of pants, an instrumented or marked shirt, an instrumented or marked article worn by the user. In yet another aspect, an equipment sensor can further include a belt sensor, a force sensor, a feet tracking sensor, or a self-contained biometric sensor adapted and configured to obtain gait parameters. In still another aspect, the gait measurement system can further include a user sensor and an equipment sensor.

In one aspect, the gait measurement system can further include a video camera. In another aspect, the gait measurement system can include one or more of an instrumented treadmill, a biological sensor for muscle activity, and a video system for monitoring and analyzing gait mechanics.

In a further aspect, the system can further include an output device for communication to a user of an integrated unweighting training system that can be one or more of a visual output device, an audible output device or a tactile device.

In an alternative aspect, the gait measurement system can provide a user's left and right heel strike data and a user's hip rotation accelerometer data to the computer controller.

In yet another aspect, an output of the computer controller sent to the display can provide an indication of DAP upper body phase coordination data. In still another aspect, the gait measurement system can provide a user's left and right load cell contact time data and the matching belt speed data to the computer controller. In one aspect, an output of the computer controller sent to the display can provide an indication of DAP cadence asymmetry data. In another aspect, a user's left and right load cell force data can be matched with a clock signal data in the computer controller. In a further aspect, an output of the computer controller sent to the display can provide an indication of DAP assisted force asymmetry data. In an alternative aspect, the differential air pressure system can include a category 1 system, a category 2 system, or a category 3 system. In yet another aspect, the gait measurement system can be adapted and configured to monitor and provide data related to user force asymmetry, user cadence asymmetry or user upper body phase coordination. In one aspect, processing can include applying a patient specific factor, a calibration factor or a metric associated with the user to a portion of the data stream. In another aspect, the collected data can include left and right load cell force data matched with a clock signal to provide an indication of DAP assisted force asymmetry data.

In a further aspect, the DAP assisted force asymmetry data can be provided to the display or a feedback indicator. In an alternative aspect, the display output can be based on or representing a portion of the limbs of the user within the differential air pressure system. In yet another aspect, the display output can further include markings to indicate desired gait motion. In still another aspect, the display output can further include a real time overlay. In one aspect, the display output can be triggered by an equipment sensor or a sensor worn on the user. In another aspect, the display output can be a triggered limited time duration video. This and other embodiments can include one or more of the following features. In one aspect, feedback provided to a user can further include one or a variety of types of biofeedback providing in conjunction with the integrated gait therapy system. In another aspect, the biofeedback can be an audible feedback signal triggered to when a user is to perform a move.

In a further aspect, the biofeedback can be an electronic stimulation sequence that starts a muscle firing sequence in the user. In an alternative aspect, the biofeedback can be a visual cue and an audible sensory stimulator triggered in synchrony with the therapy performed by the integrated unweighting and gait training system. In yet another aspect, biofeedback can include the stimulation of designated and associated action groups to help with training of a targeting muscle group. In still another aspect, providing biofeedback can include a step of causing electronic stimulation controlling one or more muscle groups as well as mechanical apparatuses that work to augment the function of one or more muscle groups the stimulation. In one aspect, the targeted stimulation area can be a muscle group. In another aspect, the targeted muscle group can be a tendon group or area. In a further aspect, while raising a leg activating a vibrator acting on a flexor and associated tendons in the lower hamstring area of the leg. In an alternative aspect, the biofeedback can include providing on or more sensory stimulators triggered in synchrony with the therapy. In yet another aspect, the sensory stimulator can provide an electrical stimulation, a vibration stimulation or another tactile stimulation. In still another aspect, the therapy can include feedback for force, cadence or phase coordination. Wherein the therapy includes training for desired cadence, training cadence or footfall pattern.

In general, in one embodiment, there is a patient worn data sensor, such as for example a shoe based sensor system for collecting and storing or transmitting data appropriate to the type of sensor to the integrated unweighted gait training system In one aspect, the integrated unweighting gait system receives the patient worn sensor data and integrates the patient worn sensor data from or collected by the patient worn sensor into a feedback loop to unweight a patient to achieve a desired gait. Thereafter, optionally, is the step of capturing additional patient worn sensor data. Thereafter the step of providing a biofeedback signal to the user based upon patient worn sensor inputs is performed when the user is using the patient worn sensor in an environment outside of the integrated unweighting gait training system. Thereafter, in some embodiments, there is a step of during an additional unweighted training session the patient worn sensor data from an environment outside of the integrated unweighting gait training system is used as part of the data in a subsequent unweighted gait therapy treatment session. In one specific exemplary aspect the patient worn sensor is a shoe sensor. In other exemplary embodiments, the patient worn sensor is any of the patient worn sensors described herein or as is appropriate for any of those listed in FIGS. 2, 3A, 3B, and 15, for example.

This and other embodiments can include one or more of the following features. In one aspect, the feedback loop can further include providing biomechanics feedback to the user for biomechanics modification.

In still other variations to an integrated gait training system, the gait measurement or parameters are provided to a controller or processor the integrated gait training system from a self-contained biometric sensor system that provides accurate, real-time measurement of a plurality of gait parameters of a user on a treadmill within the range of the sensors of the system. In one aspect, the plurality of gait parameters of a user on a treadmill are: speed, cadence, Left/Right Stride Length, and Left/Right Stride Time. In still other aspects, the plurality of gait parameters of a user on a treadmill further comprising foot placement phase asymmetry and stride time jitter.

In still another aspect there is provided a method of determining tread belt speed using an embodiment of the self-contained biometric sensor system described herein. In one specific embodiment, the sensors of the self-contained biometric sensor system are positioned over the treadmill belt so that reflectivity of the belt surface under the sensor(s) can be measured. In one specific embodiment, the sensors are an infrared emitter/detector pair (sensor). Next, applying a strip of reflective material of a precise, known length to the treadmill belt. The applying step is performed so that reflectivity of the belt surface changes dramatically while the strip is under the sensor. The type of strip and placement will vary depending upon the specific sensor type and placement on the treadmill. Next, using sensor output signals in conjunction with microprocessor clock timestamp a period of high reflectivity is used to determine the treadmill speed. In one example, if a one-foot strip of reflective material takes one second to pass under the sensor, the speed of the tread belt is 1 foot/second, or approximately 0.68 miles per hour. In further embodiments configured for higher treadmill speeds, once the system has been calibrated to the known length marker, front to front or rear to rear edge detection can also be used for greater accuracy for a given sampling rate. The method may further include input from a foot fall or foot impact sensor such as an accelerometer, load cell or acoustic sensor.

This and other embodiments can include one or more of the following features.

In one aspect, the operations of the integrated system during a user therapy session can include at least one user action recommendation or system control function related to using synthesized data.

In another aspect, the at least one action related to control using synthesized data can include the use of DAP system data or gait system data triggered from another data stream.

In a further aspect, the at least one action related to control using synthesized data can include the use of processed DAP system data or gait system data by manipulating one or more data streams.

In an alternative aspect, the at least one action related to control using synthesized data can include the use of calculated DAP system data or gait system data produced by comparing or relating two or more data streams.

In yet another aspect, the at least one action related to control using synthesized data can include the use of algorithms to produce outcomes of one or more DAP system data streams or gait system data streams In general, in one embodiment, a method of providing integrated unweighting assisted gait training for a user having impaired walking biomechanics includes unweighting the user in an appropriate unweighting system, performing a therapy routine with the user, collecting data under control of a controller or a computer processor of the appropriate unweighting system from a plurality of components of the integrated differential air pressure system during the unweighting step and the performing step, and analyzing one or more of the output data from the collecting step to determine whether to adapt the performing step. Thereafter, determining to adapt the performing step wherein an adaptive step or an adjustment step comes from a therapist, from the system or as part of a data controlled therapy. In still other aspects, the step of analyzing is done by person or by the controller of an unweighting system. Still further, after the analyzing step, optionally, there follows a step of continuing the performing step without adapting the therapy routine. Still further, after the analyzing step there follows a step of continuing the performing step after adapting the therapy routine. Other optional steps include: providing the user with feedback regarding how the user's impaired walking biomechanics are changing; repeating the unweighting, performing, collecting and analyzing steps to progressively re-train the user for walking or running with proper biomechanics; or repeating the unweighting, performing, collecting and analyzing steps to progressively proceed from a partial unweighting environment during the unweighting step to a full weight bearing environment during the unweighting step.

In one aspect, the unweighting step can be adapted and configured to provide a partial unweighting environment specific to the rehabilitation of a patient diagnosed with a disease or an injury. In another aspect, the unweighting environment can be adjusted to achieve a symmetrical walking pattern for the patient. In a further aspect, the unweighted environment can be adjusted by the user. In an alternative aspect, the unweighted environment can be adjusted by the differential air pressure system according to a predetermined protocol. In yet another aspect, the collecting step can be initiated by detecting a heel strike and triggering a video stream capture. In still another aspect, the video capture can run for a set time limit. In one aspect, a loop recorder can be used in conjunction with a high definition video stream. In another aspect, the collecting step can further include using a timing offset to trigger the capture of a portion of the high definition stream in the loop just prior to the heel strike reading. In a further aspect, the collecting step can further include storing the data stream that, optionally, can be stored for an additional timing factor after heel strike. In an alternative aspect, there is a step of cutting down the size of the collected video stream to that portion synchronized with a trigger event. In yet another aspect, there is a step of providing one or more of visual feedback, audible feedback or tactile feedback based on the analyzing step. In still another aspect, the providing step can be performed by a therapeutic stimulator. In one aspect, the providing step can be performed by a tactile stimulator, an electrical stimulation or a vibration triggered in synchrony with the therapy.

In still other aspects of the various embodiments described herein, the system processor or controller of an integrated gait training system or the processor of a self-contained biometric sensor system contains computer readable instructions adapted and configured according to system configuration for receiving, collecting and processing as appropriate under a common time stamp the data provided from the multiple data streams of the integrated gait training system or the self-contained biometric sensor system.

In still further additional aspects, the system processor or controller of a gait training system or the processor of a self-contained biometric sensor system is adapted and configured for collection of simultaneous, synthesized data from one or more components of the gait training system or the self-contained biometric sensor system. In some further aspects, the integrated gait training system includes an unweighting system. In one embodiment, the unweighting system is a differential air pressure unweighting system. In still another embodiment, the unweighting system is a non-differential air pressure unweighting system. In still further embodiments the non-DAP unweighting system is a support frame type non-DAP unweighting system or a curved arch type non-DAP unweighting system, or an unweighting arch type non-DAP unweighting system, or a monocolumn type non-DAP unweighing system or a cantilevered type non-DAP unweighting system.

In still other aspects of the various embodiments described herein, the system processor or controller of an integrated gait training system or the processor of a self-contained biometric sensor system contains computer readable instructions adapted and configured for storing, in a computer readable database stored within or accessible to the processor, the collected, synchronized or synthesized data of the unweighting system and the gait system. In some aspects, the collected, synchronized or synthesized data includes, depending upon system configuration and therapy performed data of one or more of pressure setting and control, calibration data, system type, auxiliary systems, exercise system controls, video, user worn sensor or equipment sensor, synthesized data triggered from another data stream, synthesized data from processed data from manipulating one or more data streams, synthesized data calculated by comparing or relating two or more data streams, or, optionally, synthesized data obtained using algorithms to produce outcomes of one or more data streams. In still other aspects, collected, synchronized or synthesized data is displayed, output or provided to provide real-time feedback to a user of the system. In still further aspects, there are computer readable instructions for synthesizing the system by integration of independent data streams collected into another set of data or stream of data used in conjunction with the therapy or training performed using the system. In still other aspects, collected, synchronized or synthesized data is derived from the type of patient receiving therapy and the specific system selected for his patient category (i.e., class 1, 2 or 3). In some aspects, the type of patient or system is one factor in determining the type of data synthesis applied to a specific patient therapy session or course of therapy. In still other aspects, collected, synchronized or synthesized data from one component is used to indicate the relevance of a subset of data from another component or source. It is to be appreciated that the resulting data or data stream can be presented in real time, or packaged in a way to inform another person or system or process of the state of the patient.

BRIEF DESCRIPTION OF THE DRAWINGS

The novel features of the invention are set forth with particularity in the examples that follow. A better understanding of the features and advantages of the present invention will be obtained by reference to the following detailed description that sets forth illustrative embodiments, in which the principles of the invention are utilized, and the accompanying drawings of which:

FIG. 30A illustrates a perspective view of a GaitBox.

FIG. 30B illustrates a schematic.

DETAILED DESCRIPTION

Figure 1:
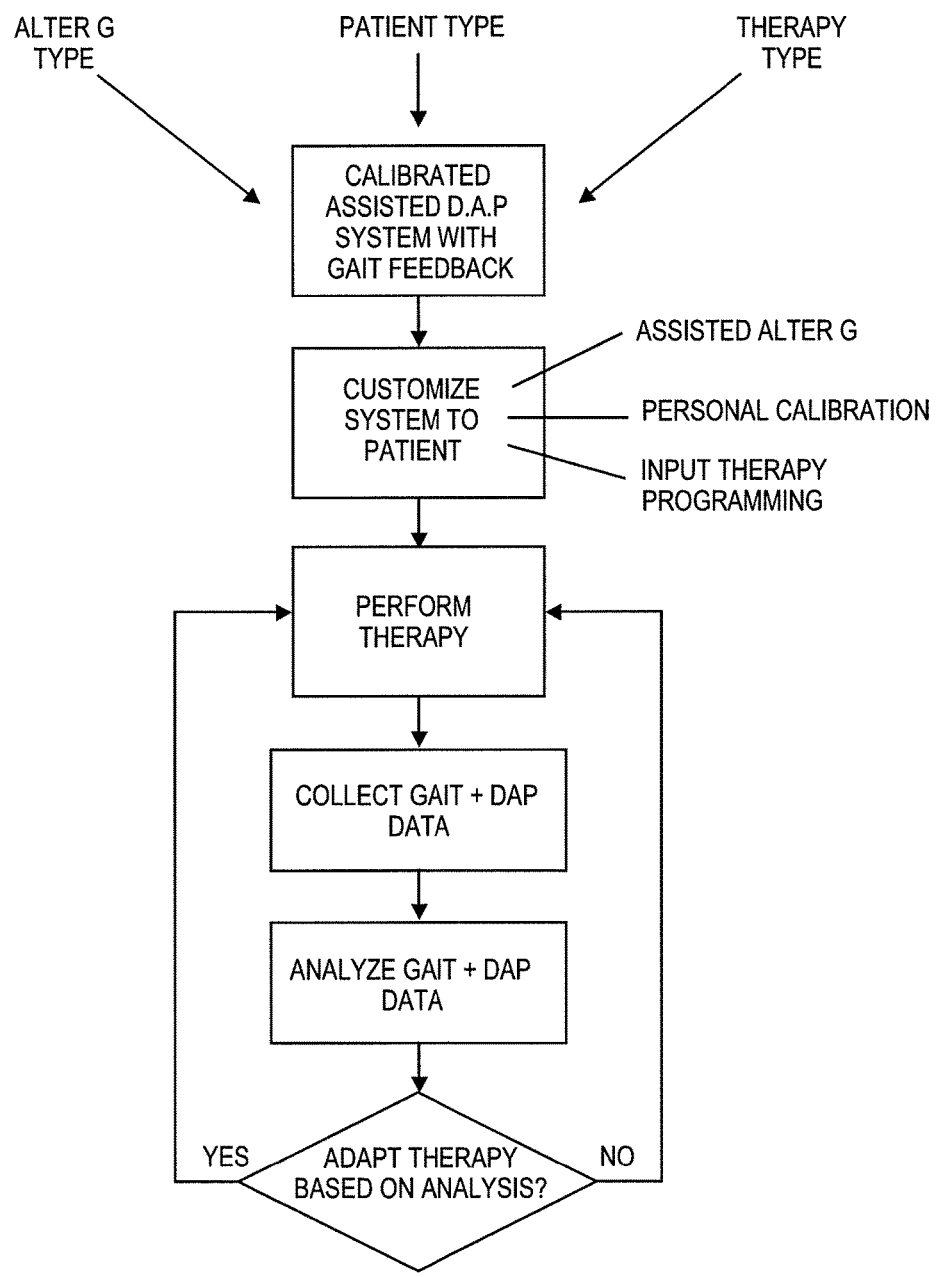
FIG. 1 is an exemplary method of providing therapy for a patient using a differential pressure system having measured gait feedback capabilities.

There are available differential air pressure systems suited to training users or patients in different categories based on a number of factors such as, for example, patient ability to access the machine, the specific training needs of the patient and the physical capabilities of the patient as well as whether the patient requires assistance during training and if so to what degree. For purposes of discussion, three basic categories will be used. Category 1 is healthy athletic with no assistance required. Category 2 is moderate assistance (post-surgical recovery) where the patient can stand in the system with assistance and remain upright. Category 3 patients require assistance for ingress/egress as well as support during therapy. A number of differential air pressure systems for various levels of patient assistance before, during or after use are described in the non-provisional patent application entitled "Differential Air Pressure Systems and Methods of Using and Calibrating Such Systems for Mobility Impaired Users" application Ser. No. 13/423,124 filed on Mar. 16, 2012 ("the '124 application"). The entirety of this application is incorporated herein by reference.

While desiring not to be bound by theory, it is believed that a patient's biomechanics will change as a result of unweighting in a differential air pressure system due to reduced pain or need for leg strength that the user may not possess due to injury, age, or illness. Further, a patient in such an unweighting environment has greater ability to intentionally change their biomechanics and gait patterns in response to feedback as compared to the ability to change gait patterns in a full body-weight loading environment. This enhanced ability of a patient to modify gait patterns in a differential pressure unloading environment is a core distinction of the current invention. Due to the greater ability in such an environment to modify gait, therapy in such an environment can be more effective than in other environments when combined with gait measurement systems and feedback systems than such gait training could be without those measurements and feedback systems and can be more effective than training with such feedback in a full-weightbearing environment in which the patient is less able to modify gait patterns. Achieving proper mechanics is an important aspect to proper rehabilitation of gait and motor training. Embodiments of the invention described herein provide systems and methods that are suited to the integration of measurements of gait and biomechanics with level of unweighting. Still further, aspects of the inventive methods described herein provide for specific rehabilitation protocols integrating biomechanics measurements with unweighting which are believed to provide more effective and more precise rehabilitation as compared to conventional visual assessments by the therapist or patient during unweighting rehabilitation and more effective and more precise rehabilitation than with biomechanics measures in a full bodyweight environment or alternate unweighting environment such as a pool or harness in which gait mechanics are significantly altered by the unweighting system.

This application will describe the integration of one or more gait measurement systems for use with a differential air pressure system. Integrated training systems such as these will provide a greater variety of controlled training and therapy for patients of all patient categories. Impairment to a patient's ability to complete or participate fully in gait training may come from a number of sources. For example, a patient with a neurological disorder may have motor impairment along with muscle weakness. One aspect of off-loading a patient using the inventive systems described herein permits the use of differential pressure assistance to unload the patient to reduce the impact of the impairment due to weakness. In another example, a patient recovering from orthopedic surgery may experience pain when exercising with full weight. While this patient may physically be able to modify their gait at full weightbearing where a weak patient may not, the reduction of pain allows for the patient to mentally cope with some necessary mechanical corrections that need to be made. Another aspect of off-loading a patient using the inventive systems described herein permits the use of differential pressure assistance to unload the patient to reduce the impact of the impairment due to pain. These are two examples of how a DAP system with integrated gait capabilities can assist in controllably and reliably removing common barriers to gait training.

Embodiments of the present invention provide for the integration of a pressure assisted unweighting environment with biomechanics and gait measurements and a range of therapies for gait improvement. Gait training and biomechanics are commonly evaluated in order to assess walking and running dynamics and to assist patients or athletes in improving their mechanics. Embodiments include a range of devices such as instrumented treadmills, biological sensors for muscle activity, and video systems for monitoring and analyzing gait mechanics. One or more of these gait measurement systems are training devices that are integrated with a differential air pressure system to provide a controlled, repeatable unweighting environment for gait and walking or running mechanics. Embodiments of the present invention provide a system to retrain individuals to improve or alter walking or running mechanics by unweighting the individual in a differential air pressure environment and simultaneously measuring one or more parameters of gait or biomechanics such as stride length, ground reaction force, lateral movement of knees, angles of knees and ankles, forefoot or heel strike parameters, muscle activation patterns, or movement symmetry.

In many patients, the parameters described above are suboptimal at full weightbearing walking or running. For example, a patient with recent orthopedic surgery in one lower limb, such as total knee arthroplasty will typically walk with asymmetric motion. In an unweighting environment, such a patient can walk with greater symmetry due to reduced pain. Retraining symmetry in walking can be important in speeding the recovery of function in such a patient and reducing risk of future injury due to the asymmetry of gait in such a patient. Embodiments of the differential air pressure assisted gait training methods herein provide an effective method of retraining symmetry of mechanics and gait to enable the patient to practice walking symmetrically, providing feedback to the patient when such symmetry is achieved and when it is violated.

One specific aspect of treatment using this methodology is to unweight the patient and measure biomechanics, determine at what level of unweighting the desired mechanics of gait and motion can be achieved, and then provide feedback to the patient, athlete, trainer or physical therapist on an ongoing or periodic basis. Such feedback would enable recognition of proper mechanics and would reinforce more time walking or running with proper mechanics. More time spent walking or running with proper mechanics would retrain muscles in proper motion and would drive neuroplasticity to train such proper motion. Over time, as the desired gait mechanics are achieved with more consistency, the amount of unweighting may be progressively reduced in order to acclimate the user to walking or running in this new method of gait patterns until such patterns are set as new biomechanics at full gravity.

In still further additional treatment methodologies, electrical stimulation of muscles, braces to align joints, powered exoskeletal support, and other established gait training and muscle training methods may be integrated into progressive unweighting and reloading protocols to facilitate the gait training. These standard methods of gait training may be more effective when modified for performance in an integrated gait and differential air pressure environment of unweighting, where proper biomechanics can be achieved more readily for patients than in a full gravity environment.

In one aspect there is provided a differential air pressure and gait training system to improve gait training in patients with impaired biomechanics by enabling the patient to walk or run in a partial unweighting environment with feedback regarding how the patient's biomechanics are changing, so that the patient can retrain walking or running with proper biomechanics and then gradually apply this new training progressively back to a full weightbearing environment.

In another aspect, there is provided a differential air pressure and gait training system that enables exercise and rehabilitation of patients from disease or injury in a partial unweighting environment with biomechanics and gait feedback to reduce risk of further injury and to enable improvement of the rehabilitation protocols. In one specific example, a patient with hip fracture could exercise and walk through their rehabilitation program at the right level of unweighting to enable symmetrical walking so that they learn to walk properly, rather than learning to walk in a manner that compensates for the injured side and therefore exposes the patient to progressive further injury due to the asymmetrical walking pattern.

FIG. 1 is an exemplary method of providing therapy for patient using a differential pressure having measured gait feedback capabilities.

First, with an understanding of the different types of differential pressure systems available, the patient type to use the system, and the desired therapy to be performed, select an appropriate system to perform therapy with a user. A number of systems types for categories 1, 2 and 3 are provided in the '124 application. A category 1 system includes for example FIG. 2A of the '124 application. A category 2 system includes for example FIG. 7A of the '124 application. A category 3 system includes for example FIGS. 1A and 19 of the '124 application.

Next, customize the system to this patient. Customization may take on many forms such as based on the specific type or configuration of the differential air pressure system being used, personal calibration techniques, or inputs of specific patient parameters, or protocols or patient specific training goals.

Next, the user performs the therapy in the system according to the input program or protocol.

Next, the system will collect gait and differential pressure and other system parameters while therapy is ongoing.

Next, the system will analyze the collected data.

Next, determine whether to adapt the therapy based on the prior analysis step. One result of this step is to adapt the therapy and continue to perform the therapy as adapted. Another result is to continue to perform therapy without adapting the therapy based on the analysis.

Figure 2:
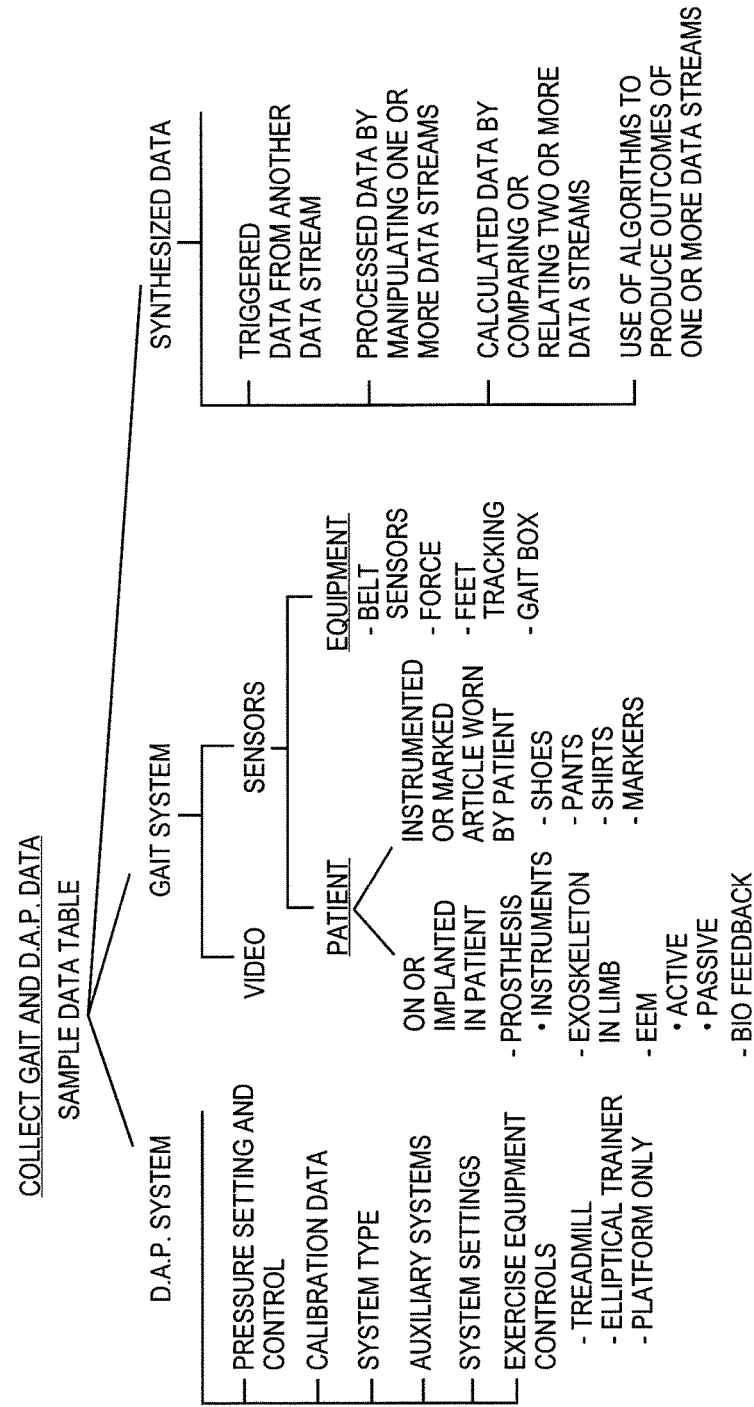
FIG. 2 is an exemplary data collection table or summary of data inputs in an exemplary integrated differential pressure control system having gait measurement capabilities.

One example of the format of a data table for an integrated differential air pressure and gait measuring and training device is show in FIG. 2. This representative data system envisions collection and synthesis of data from several data streams depending upon the specific configuration of the system being used for therapy. The contents of FIG. 2 (i.e., the data table or variables collected, controlled, processed or manipulated by the control system) will vary to the degree needed to include collection of the various continuous, nearly continuous or segmented data streams including synthesized data from the therapy system.

Figure 26:
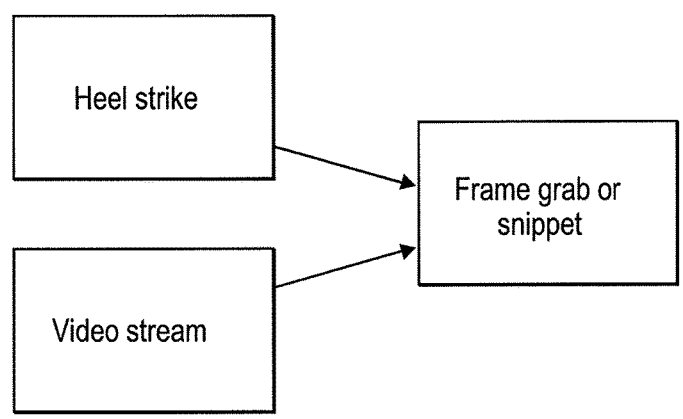
FIG. 26 is an example of a two element data synthesis in an integrated differential air pressure and gait training system.

Simultaneous data collection refers to the general process of collecting data from multiple data streams under a common time stamp. It is to be appreciated that embodiments of the various inventive differential pressure assisted gait training systems described herein are adapted and configured for this purpose. However, the various inventive systems are also adapted and configured to synthesize the data that is being collected from the systems, subsystems, accessories, and sensors as shown in the exemplary data table (See FIG. 2). As used herein, synthesis of data refers to the integration of the independent data streams collected into another set of data or stream of data used in conjunction with the therapy or training undertaken in the system. Synthesis goes beyond basic data collection in that the data is put together to straight-forwardly assist the patient or therapist understand the workout from a quantitative standpoint. Data collection systems just record data, but do not take steps towards helping a patient or therapist who do not have training or experience with the direct data being collected. In one alternative, the type of data synthesis is derived from the type of patient receiving therapy and the specific system selected for his patient category (i.e., class 1, 2 or 3). As such, the type of patient or system is one factor in determining the type of data synthesis needed for a specific patient therapy session or course of therapy. In still further alternatives, the data collected from one component is used to indicate the relevance of a subset of data from another source. In one specific example, there is a camera providing a high definition video stream of a post knee surgery patient's knee movement during therapy. The storage and later processing requirement for such a high volume of data may be a difficult and time consuming task. In one specific example of data synthesis, a force sensor on a treadmill is used to indicate heel strike and triggers the capture of a video stream that runs for a set time limit. In another specific embodiment, there is also a loop recorder used in conjunction with the high definition video stream. In this example, the heel strike sensor, employed in conjunction with a timing offset, is used to trigger the capture of a portion of the high definition stream in the loop just prior to the heel strike reading. Thereafter, the data stream is stored for an additional timing factor after heel strike. During the use of this data, the relevant portion of the video is now cut down to and synchronized with the recording or relevant trigger, here a heel strike reading in this example. FIG. 26 illustrates the selective combination of heel strike data with video stream data to represent the collection of frame grab or snippet of DAP and gait data. The data or datasteam can be presented in real time, or packaged in a way to inform a doctor, therapist, shoe maker, etc. of the state of the patient.

In still another example, a self-contained biometric sensor system—referred to herein as GaitBox—is another form of Gait system sensor that may be employed according to the various Gait techniques described herein. The GaitBox provides accurate, real-time measurement of basic gait parameters on any treadmill. The basic gait parameters are: Speed (distance divided by time); Cadence (number of steps per minute); Left/Right Stride Length (distance between successive impacts of same foot, e.g. left-foot-impact to left-foot-impact); and Left/Right Stride Time (time between successive impacts of same foot). Other additional gait parameters include, by way of example and not limitation, foot placement phase asymmetry (right to left step time compared with left to right step time) and stride time jitter (variation in timing between subsequent footfalls on the same or opposite sides).

Figure 3:
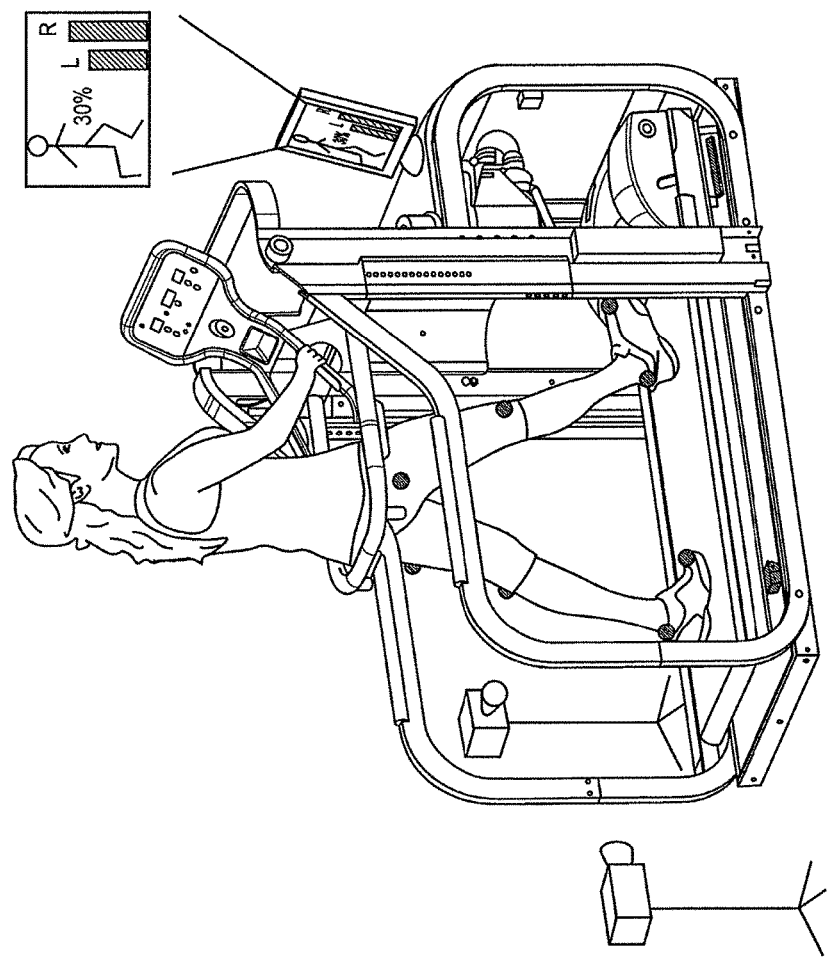
FIG. 3 is an isometric view of a differential air pressure training system having integrated gait capabilities and a performance feedback monitor.
Figure 3A:
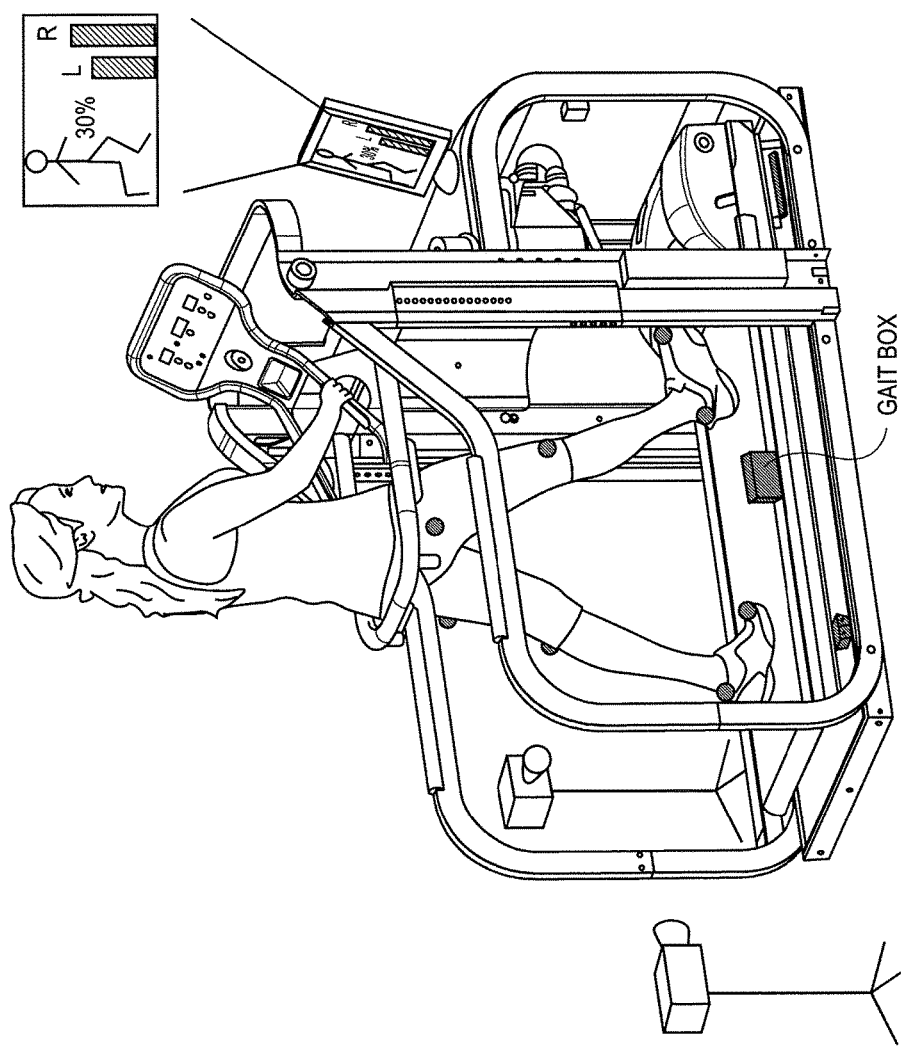
FIG. 3A illustrates the system of FIG. 3 with a GaitBox shown in position on the treadmill frame.

A GaitBox is shown on the treadmill frame in FIG. 3A. Additional details of GaitBox as set forth below with regard to FIGS. 30A and 30B.

Figure 27:
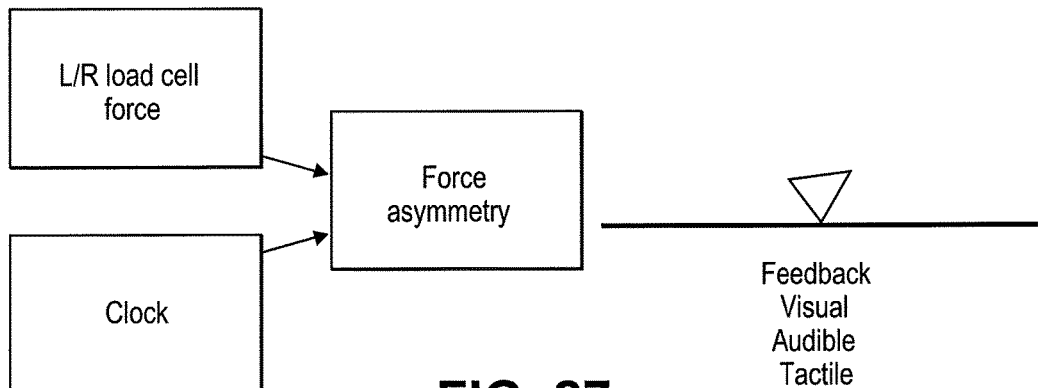
FIGS. 27-29 are examples of two element data synthesis in an integrated differential air pressure and gait training system that also include a display with optional additional feedback that is visual, audible or tactile.

Other more advanced types of synthesis are also performed by embodiments of the inventive system. In another exemplary system a data stream that is being collected may be processed prior to or in conjunction with recording. Here, processing may take on a number of different forms such as applying a patient specific factor such as a calibration factor or other metric associated with a specific patient. One example of a kind of data synthesis is shown in FIG. 27. FIG. 27 illustrates how the left and right load cell force data may be matched with a clock signal to provide an indication of DAP assisted force asymmetry data. The DAP assisted force asymmetry data is then provided to the user in a simple display or other feedback technique such as the indicator shown on the right side of FIG. 27. The placement of the arrow in the middle is the desired location. As the user trains, the detected force asymmetry will cause deflection of the arrow. As the patient alters his gait, the arrow moves in a corresponding direction.

Figure 28:
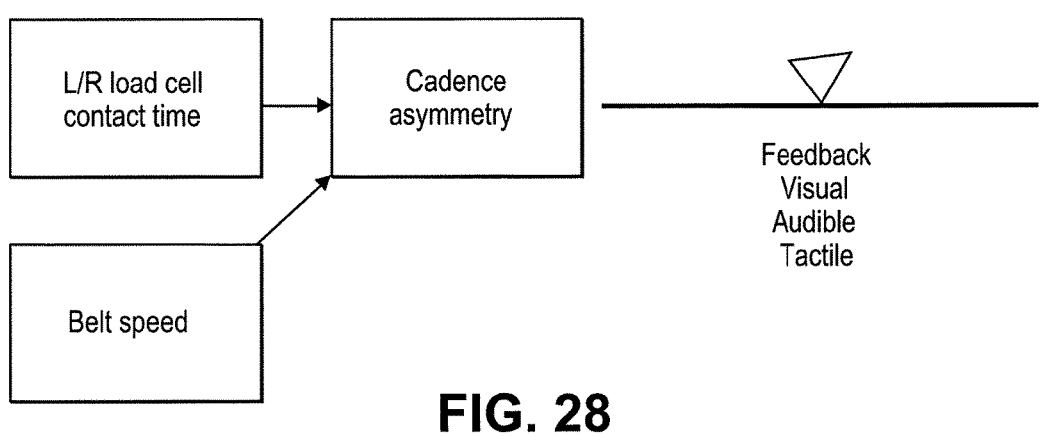

Another example of a kind of data synthesis is shown in FIG. 28. FIG. 28 illustrates how the left and right load cell contact time data may be matched with belt speed data to provide an indication of DAP cadence asymmetry data. The DAP assisted cadence asymmetry data is then provided to the user in a simple display or other feedback technique such as the indicator shown on the right side of FIG. 28. The placement of the arrow in the middle is the desired location. As the user trains, the detected cadence asymmetry will cause deflection of the arrow. As the patient alters his gait, the arrow moves in a corresponding direction.

Figure 29:
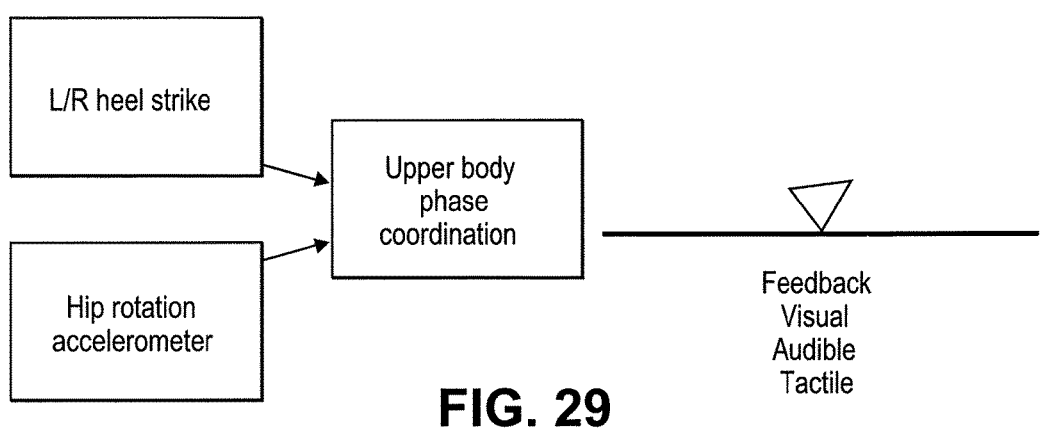

Another example of a kind of data synthesis is shown in FIG. 29. FIG. 29 illustrates how the left and right heel strike data may be matched with a hip rotation accelerometer data to provide an indication of DAP upper body phase coordination data. The DAP upper body phase coordination data is then provided to the user in a simple display or other feedback technique such as the indicator shown on the right side of FIG. 29. The placement of the arrow in the middle is the desired location. As the user trains, the detected upper body phase coordination data will cause deflection of the arrow. As the patient alters his body phase coordination, the arrow moves in a corresponding direction.

Another form of processing may be the application of use factors, calibration settings or auxiliary component settings applied to data streams based on the kinds of specific systems, auxiliary systems or components utilized in a specific training scenario. In this way, data can be collected in a raw form as well as with normalization factors to standardize data collected from different sensors, components or patient settings. Thusly, data collected for different patients using similarly configured systems but with different components may have data collected that will permit the patient specific data to be compared and/or aggregated for wide spread data collection. Consider this specific example. A normalizing factor would be the factor used where a CAT 2 training system with a shoe sensor from vendor A and a post-surgery knee male in Toledo and a CAT 2 training system with a shoe sensor from vendor B with a post-surgery knee male in Topeka will each record the respective patient's own raw data but there will be corresponding normalized data that eliminates the variations (if any) between the sensors from different shoes and different vendors. In a similar way, where needed based on specific circumstances, all or some of the components in the system (See FIG. 2) may be processed such that a common or normalized data setting may be applied so that when data is collected from systems with different specific components, the data streams may include both raw and normalized. In one specific embodiment, the application of one or more normalization factors is one kind of data synthesis.

In still another type of data synthesis, the data from one or more data streams may be used in calculations or further processing to yield a determination or outcome related to the input data streams or according to the therapy being undertaken. One example is the use of an algorithm to perform transformations of one or more data streams. The output of these functions will be stored along with the other recorded data. In still another example, an algorithm may include various weighting factors to a data stream such that some data may be processed in a manner consistent with the type of therapy being delivered. In still further specific examples, a processing algorithm may include fuzzy logic or artificial intelligence using a computer processor adapted and configured for that purpose.

Current state of the art therapy uses DAP technology to unweight a patient while the physical therapist provides feedback by viewing the patient as they work out. Some systems incorporate a video feedback element that allows the patient to view themselves from various angles. By using only one type of feedback, there may be optimal treatments that are left unidentified by the therapist. By integrating multiple measurement systems with a DAP system, synthesizing the data streams, and presenting the information in an appropriate way, a therapist would have the ability to utilize information that has only been able to be gathered in a laboratory setting in the past. The therapist would have the ability to then analyze and more effectively set workouts for the patient to improve recovery time.

FIG. 3, for example, illustrates a patient a using a DAP system with cameras, ground force sensors, and inertial sensors on the user's legs and hips. In this view, the pressure bag that normally covers the frame and defines the pressure chamber is removed to permit the interior details of the pressure chamber and the instruments contained therein to be observed. Throughout the workout, the system takes data about the user's gait, speed, incline, and effective bodyweight. That information is synthesized and given to the therapist during or at the end of the workout. In one alternative, the therapist can then watch a video that shows the patient's movements, speed, weighting, and the angles of the hips at each point. The therapist can use that information to more effectively set the next workout, leading to better recovery times. Due to the placement of the sensors, biomechanics points such as the user's hips, that are not visible through the enclosure of a current DAP system, can be measured, tracked and evaluated.

Figure 4:
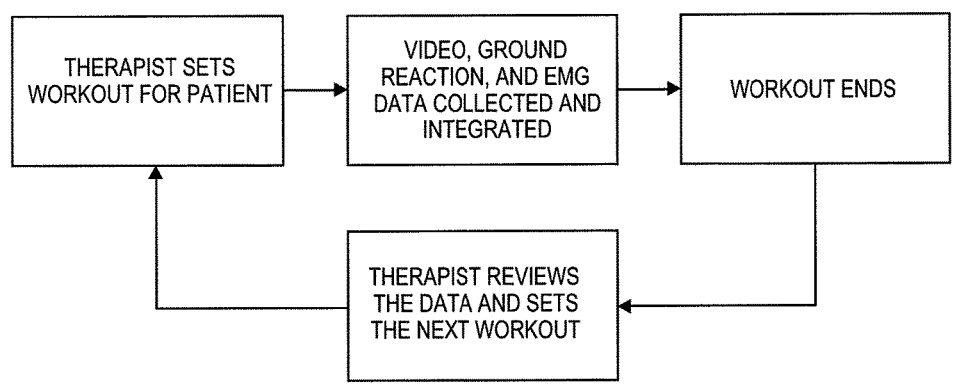
FIG. 4 is an exemplary specific workflow of a therapy and training process.
Figure 5:
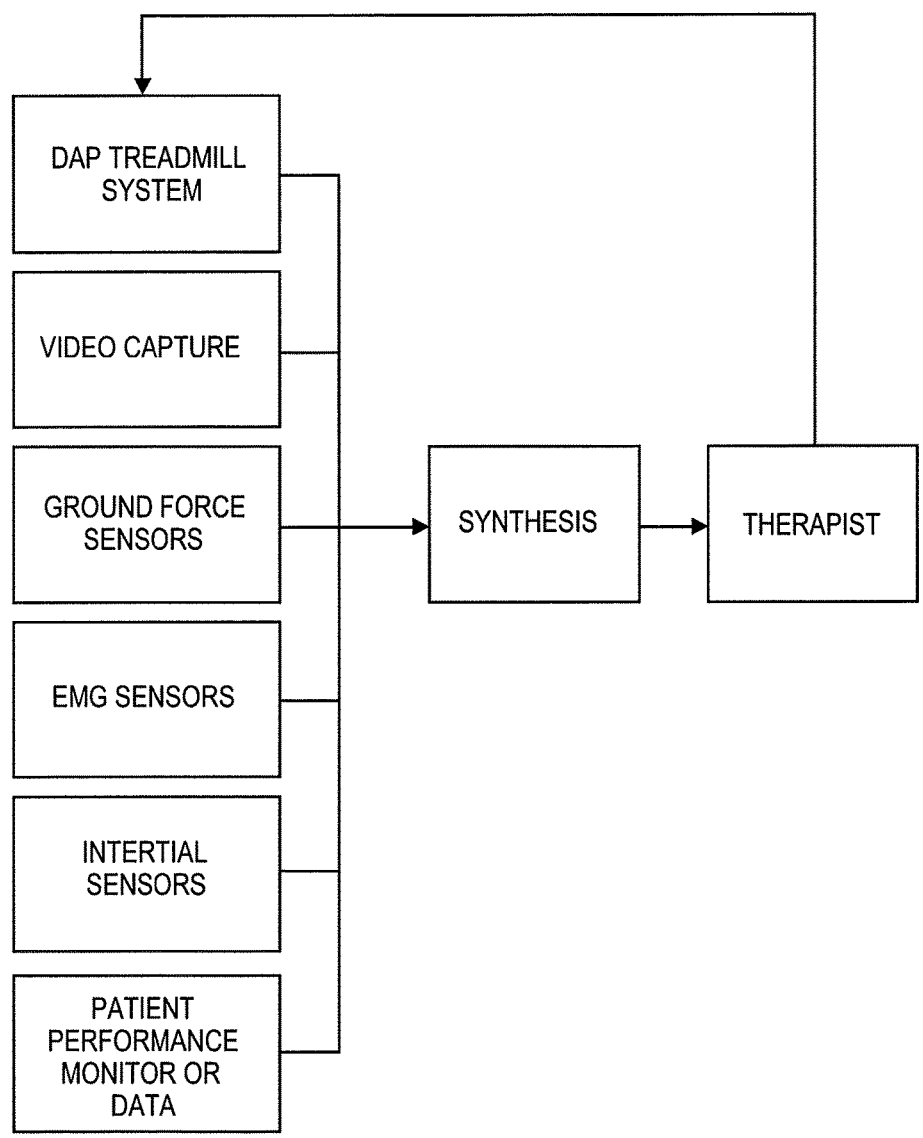
FIG. 5 is an exemplary multi-sensor data stream and synthesis flow for the workflow described in FIG. 4.
Figure 6:
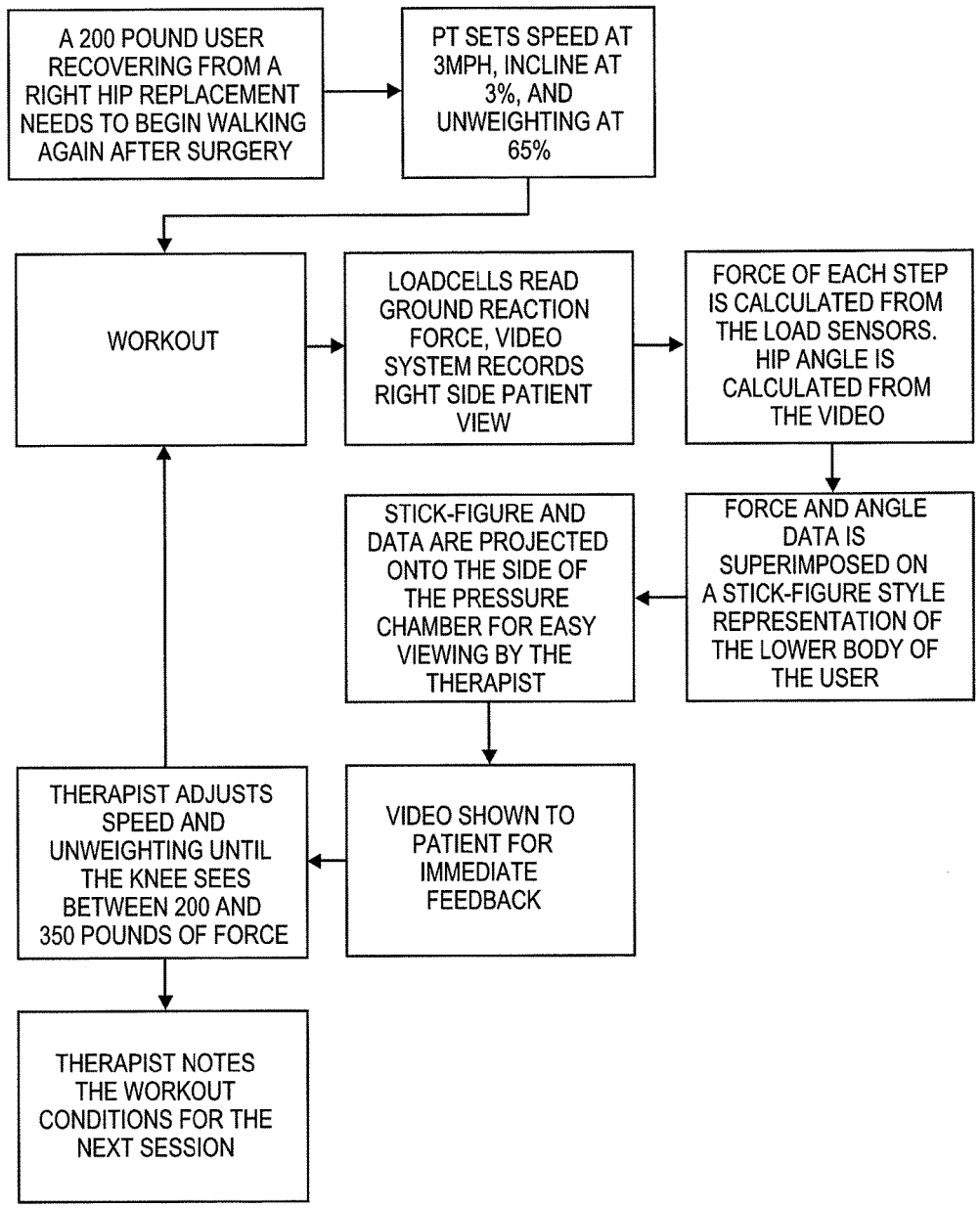
FIG. 6 is a specific patient training example for the system and technique described in FIGS. 3 and 4.

FIG. 4 illustrates a more specific work flow of the therapy and training process described. FIG. 5 is an exemplary data stream and synthesis flow for the above described example. FIG. 6 is a specific patient training example for the above described system and technique of training.

While the method of FIG. 1 provides a general procedure for conducting therapy using differential pressure and date measurement feedback, there are alternatives to be provided by the therapy system. These alternative outcomes based on the "adapt therapy" step will now be discussed from a manual feedback to a generally increasing automatically controlled feedback system. It is to be appreciated that while these alternative feedback mechanisms are described as discrete separate configurations, the system may adapt any or all of these feedback mechanisms for any particular user, specific training session, or ongoing therapy protocol.

Figure 7:
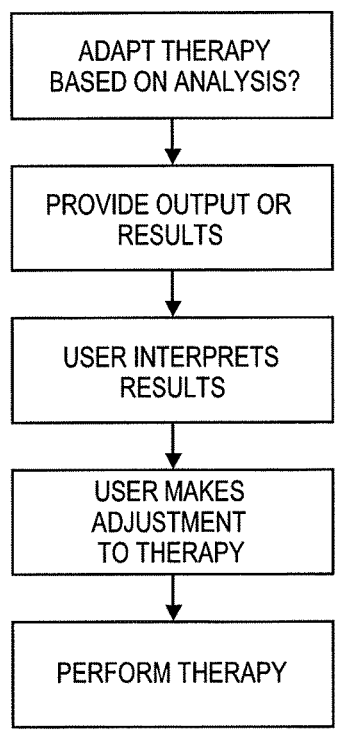
FIG. 7 is a flowchart of one alternative outcome based on the adapt therapy step from the method of FIG. 1.

FIG. 7 describes one alternative outcome based on adapt therapy step. In this outcome the system provides an output of results. Next the user will interpret the output of results. Then, the user makes an adjustment to the therapy system based on the user's interpretation of the results. Thereafter, the therapy session will continue or be set for the next training session.

Figure 8:
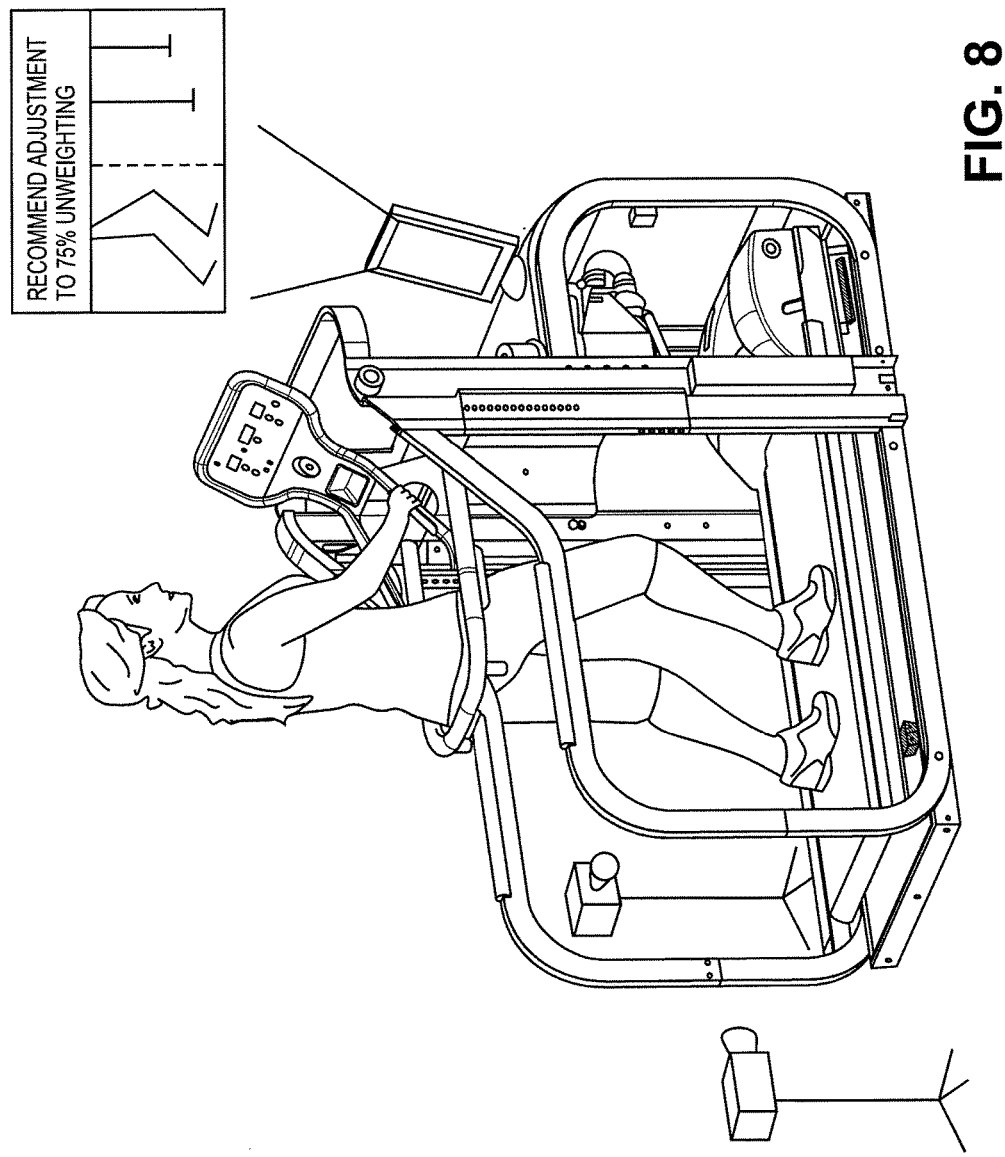
FIG. 8 is an isometric view of an exemplary system using multiple gait analysis tools to provide real-time feedback on a display to a patient.

FIG. 8 illustrates one exemplary system using multiple gait analysis tools and DAP to provide real-time feedback to assist patients and therapists. In this view, the pressure bag that normally covers the frame and defines the pressure chamber is removed to permit the interior details of the pressure chamber and the instruments contained therein to be observed. To help the therapists identify better treatments, incorporating an analysis aspect into the first system would allow the therapists to receive real-time input on ways to improve the workout from a quantitative standpoint. The state of the art treatments now use either video feedback or force sensors with DAP to show the therapist or patient limited aspects of their gait. By integrating and synthesizing multiples sensors and measurement systems together, and providing analysis, the patients and therapists will be able to more accurately and thoroughly judge and correct or modify gait in a desired fashion.

That system can be extended to include feedback from other sensors used to capture gait, workout parameters, other physiological measurements, or psychological elements according to specific system, component, therapy or patient requirements. Integrating data from, for example, EEMG sensors and inertial sensors into understandable information would give a depth of information to a patient or therapist to adjust their gait with the assistance of unweighting that does not exist today. Further, in a DAP environment, such data is more useful to a patient and therapist than it would be in a full weightbearing environment because of the greater ability of the patient to adjust gait mechanics in the DAP environment. Similarly, the DAP environment permits greater ability to adjust gait desirably in response to these inputs than does an alternate environment such as pools or harness systems in which the gait measurements would be altered by the forces and restrictions placed on the user by the harness or pool environment and the ability of the user to adjust gait is less in such environments than in a DAP environment.

Figure 9:
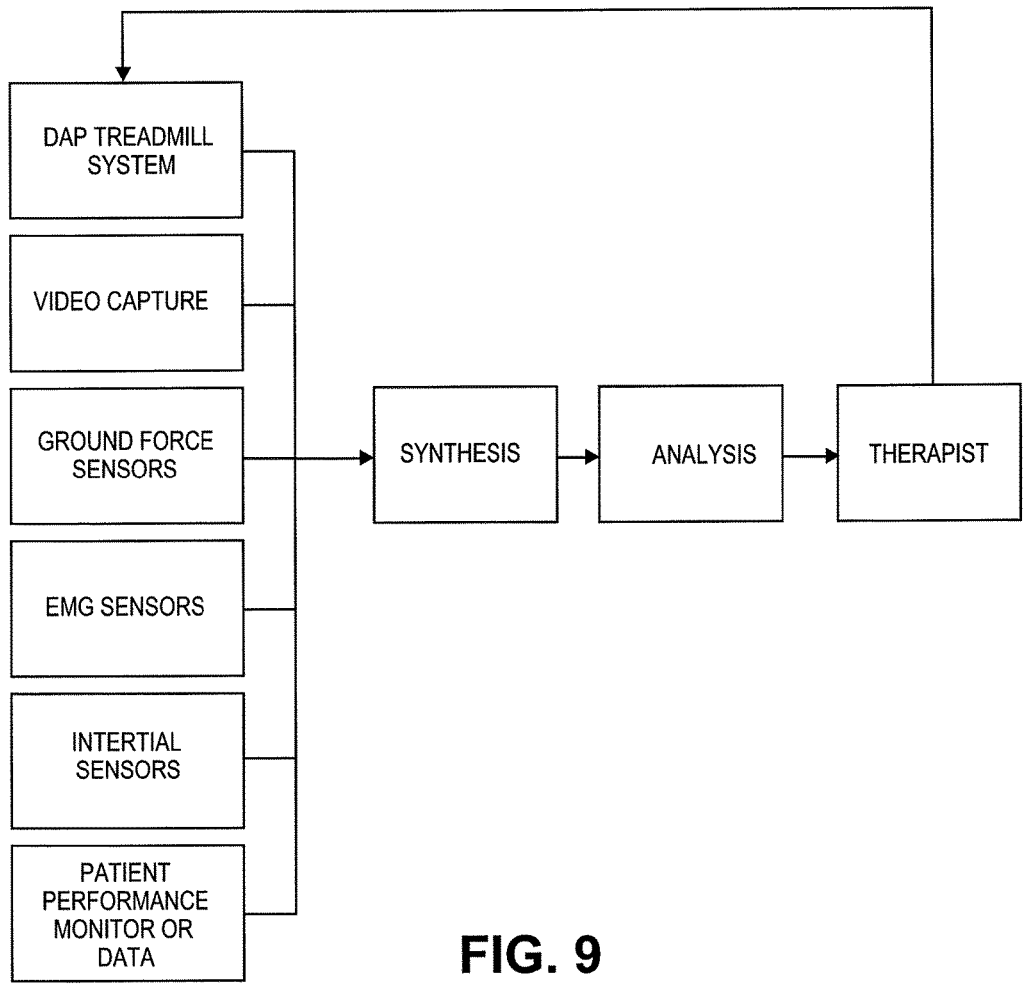
FIG. 9 is an exemplary data collection, synthesis and information processing flow for the system of FIG. 8.
Figure 10:
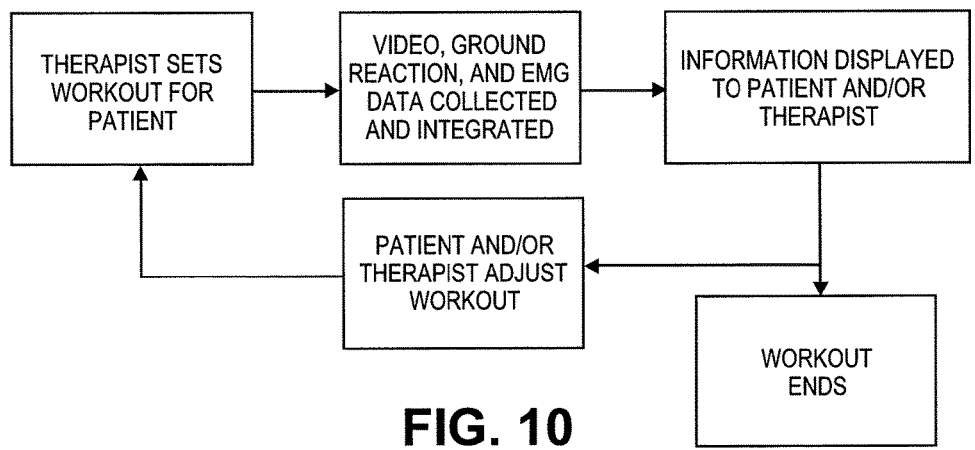
FIG. 10 is an exemplary work flow.
Figure 11:
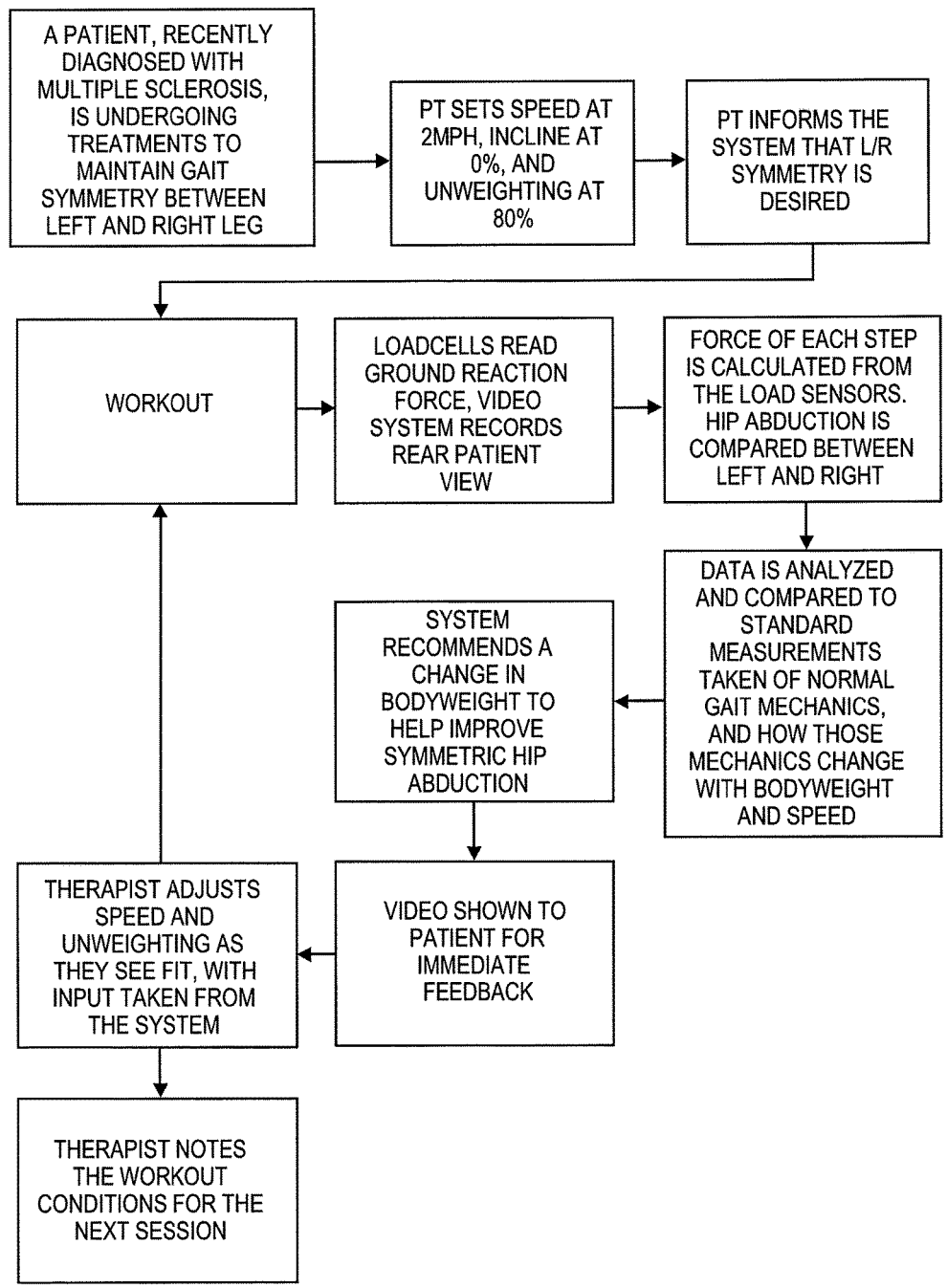
FIG. 11 is a specific patient example using the work flow and method of FIG. 9.

FIG. 9 illustrates an exemplary data collection and information processing flow for this specific system configuration and therapy example. FIG. 10 illustrates one exemplary work flow scenario. FIG. 11 is one example of a patient specific therapy procedure using the system and methods above. The patient in this example would likely use a category 2 or category 3 system as described in the '124 application.

Figure 12:
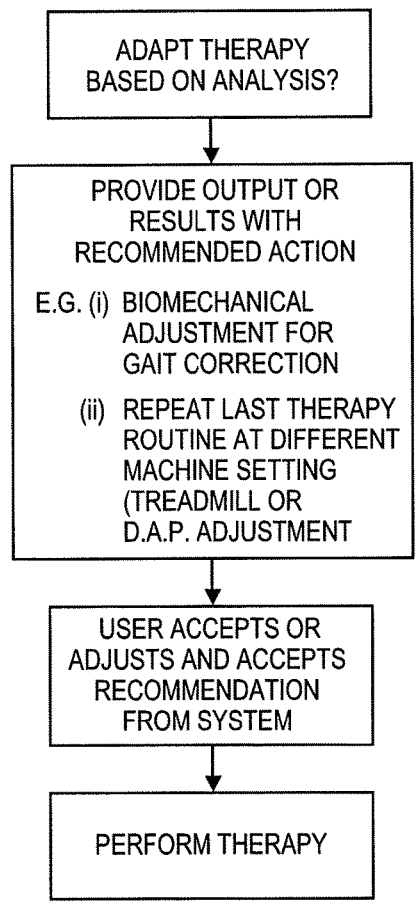
FIG. 12 is an additional alternative process for adjusting gait therapy.

FIG. 12 differs from FIG. 7 in the outcome based on the adaptive therapy step in that the system will now provide a recommendation for gait correction. In this alternative outcome, the system provides an output or results with a recommended action. Exemplary recommended actions might be a biomechanical adjustment for gait correction. For example, the system may indicate for the user to change the orientation of their foot, rotate their ankle, bend their knees more, or other adjustments that are based on analysis of the patient gait data to correct or modify that patient's gait. Another exemplary representative recommended action would be for the system to recommend repeating the last gait therapy routine however at a different amount of differential pressure assist. For example, in one possible embodiment, if a desired gait pattern were achieved at a certain degree of unweighting, the system could recommend to the patient every few minutes to slightly increase the amount of loading by unweighting less in order to find the point at which desired mechanics patterns are no longer maintained. This would permit precise determination of the unweighting level needed to train proper mechanics for this patient. Other recommended actions are possible based on the specific patient performance and performance parameters entered into the treatment system. The user next is allowed to accept or reject the recommended action or to accept with modification the recommended action from the system. Thereafter the system performs the therapy either as a next segment of training or in a subsequent training session.

Figure 13:
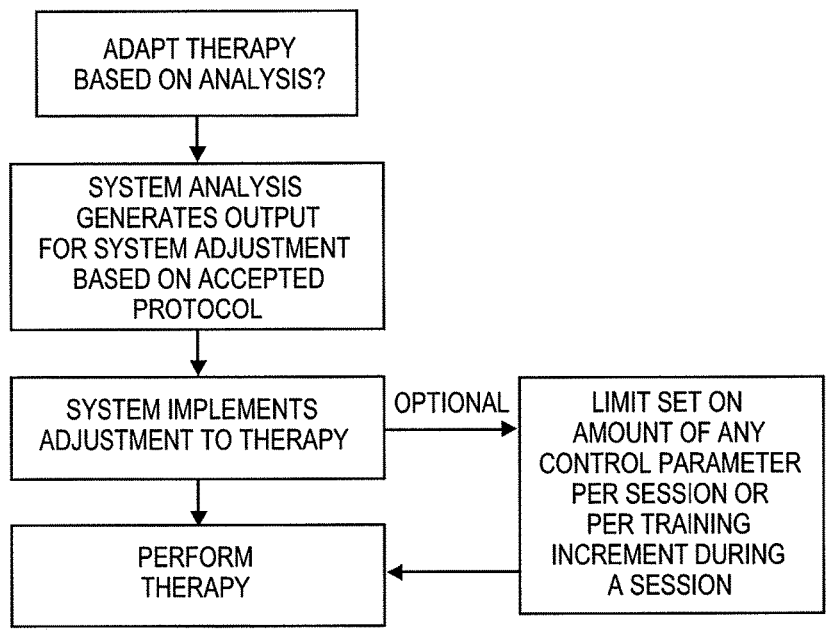
FIG. 13 is an additional alternative process for adjusting gait therapy in a differential air pressure training environment.

FIG. 13 differs from FIG. 12 in that the outcome based on the adaptive therapy step is more automated in the system's response to the users performance. Here again the analysis is performed based on the collected data and the patient performance. The system analysis will generate an output for the system adjustment based on the accepted protocol. Here this protocol might be for specific postsurgical training, gait correction, or other patient specific therapy endpoints. A significant advantage to this type of system is that it will be able to modify gait in ways a therapist could not. As an example, research may show that attempting to develop a slightly asymmetrical gait in a DAP environment produces better results at full weightbearing. The system would be able to adjust speed, incline, and bodyweight between left and right footplants, or plant vs. pushoff stages of walking or running. A therapist would not be able to control a system that quickly and accurately, where a fully automated system could. Next, the system will implement the adjustment to the therapy and the therapy session will proceed in the next segment of treatment or in the next session of treatment. Optionally, the system's ability to implement an adjustment to the therapy is limited. This limit is set on the amount that a control parameter can change per session or per training increment during a session. In this way, the system may be able to only change the system parameters within an established safe limit of parameter change for this patient type, age, previous performance, established protocol, or other safety related parameter for system adjustment.

Figure 14:
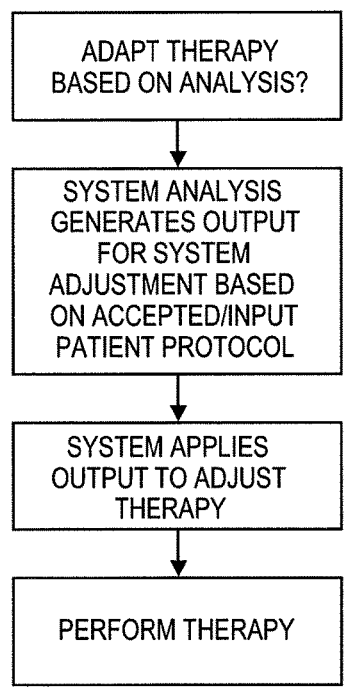
FIG. 14 is an additional alternative process for adjusting gait therapy in a differential air pressure environment.

FIG. 14 differs from FIG. 13 in that the outcome based on the analysis is generated by and automatically implemented by the system. This version of the system provides integrated and automated correction of gait therapy and differential pressure support parameters based on patient performance, gait data collection and analysis, and specific inputs of a patient training protocol. Here again the adapt therapy step is based on the prior analysis of collected data and review of patient performance and other parameters. The system analysis will generate an output for system adjustment based on the patient protocol. The system output and adjustment will be applied to the system during therapy with or alternatively without notice to the user depending upon patient specific training parameters. Thereafter, the therapy will continue using the adjusted system parameters.

Figure 15:
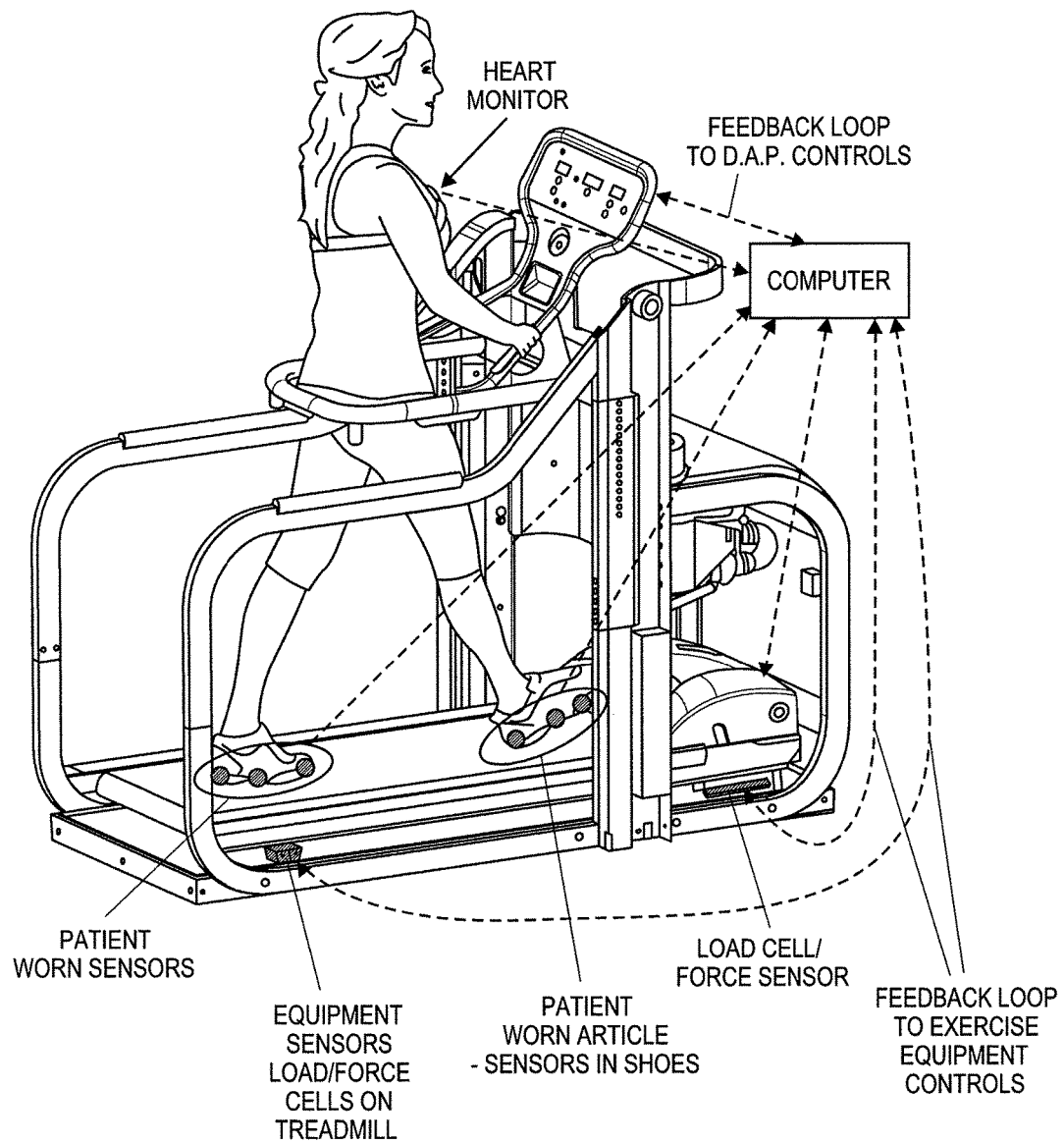
FIG. 15 is an isometric view of a differential air pressure training system have additional gait data measurement devices.

FIG. 15 illustrates a system using gait analysis tools to directly control workout parameters. In this view, the pressure bag that normally covers the frame and defines the pressure chamber is removed to permit the interior details of the pressure chamber and the instruments contained therein to be observed. If the analysis of the incoming sensor data is appropriate, the system can be extended to directly control workout parameters to automatically optimize a therapy session to improve specific aspects of gait. The system would take input from the sensors such a EMG, video, inertial, and ground force; then evaluate what workout parameters (effective bodyweight, speed, incline, balance, etc. . . . ) need to be adjusted to optimally improve the patient's gait. The system can also monitor the gait changes observed during the session to determine if the desired improvement is achieved and test alternate parameter settings within allowed ranges while providing feedback to the patient to assist in guiding patient-directed gait modification attempts while measuring the changes in gait patterns made in response to this feedback. The feedback loop between the patient, the system's sensors, the changes in workout parameters, and the methods of directing gait changes can iteratively interact to enable desired gait modification to be achieved. This allows a patient to recover more quickly, and allows a therapist to concentrate on other aspects of patient health improvement.

Therapists would be enabled to set bounds for how much the workout parameters can change, so as not to cause an injury or overwork the patient. Limitations on particular aspects of the therapy could also be accessed from a database based on research, a physician's recommendations based on the procedure or from a database of comparable patent and/or system configurations therapies and outcomes. Therapists would also be enabled to set specific desired gait parameter changes or targets desired so that the feedback process could be directed by the system to reinforce and enable incremental improvements toward the desired gait mechanics patterns.

Figure 16:
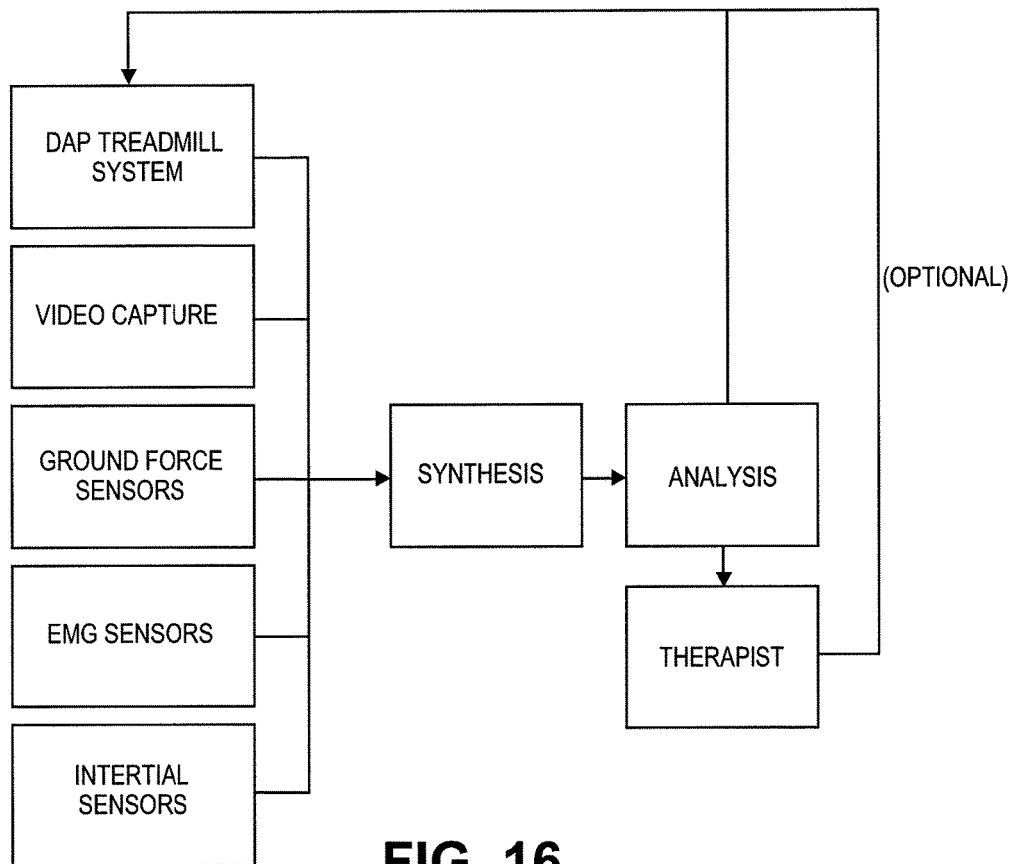
FIGS. 16 and 17 are information collection and work flow examples for the use of the system in FIG. 15.
Figure 17:
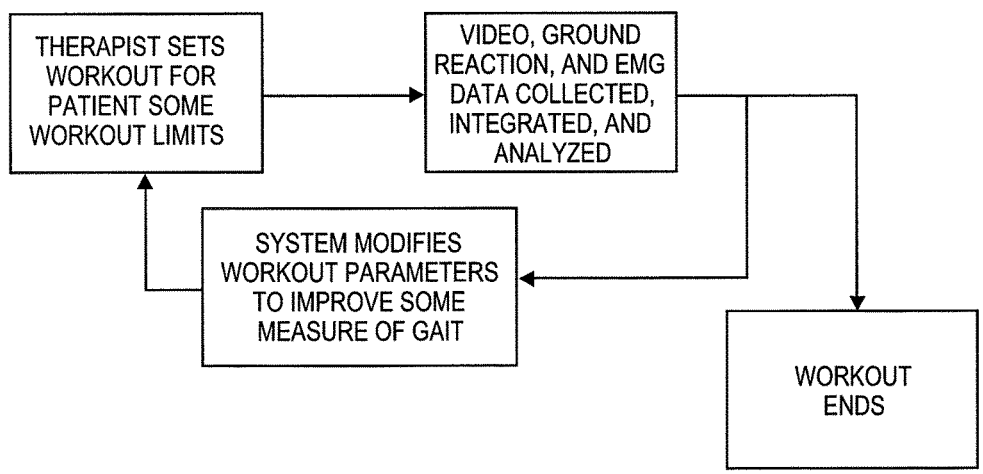
Figure 18:
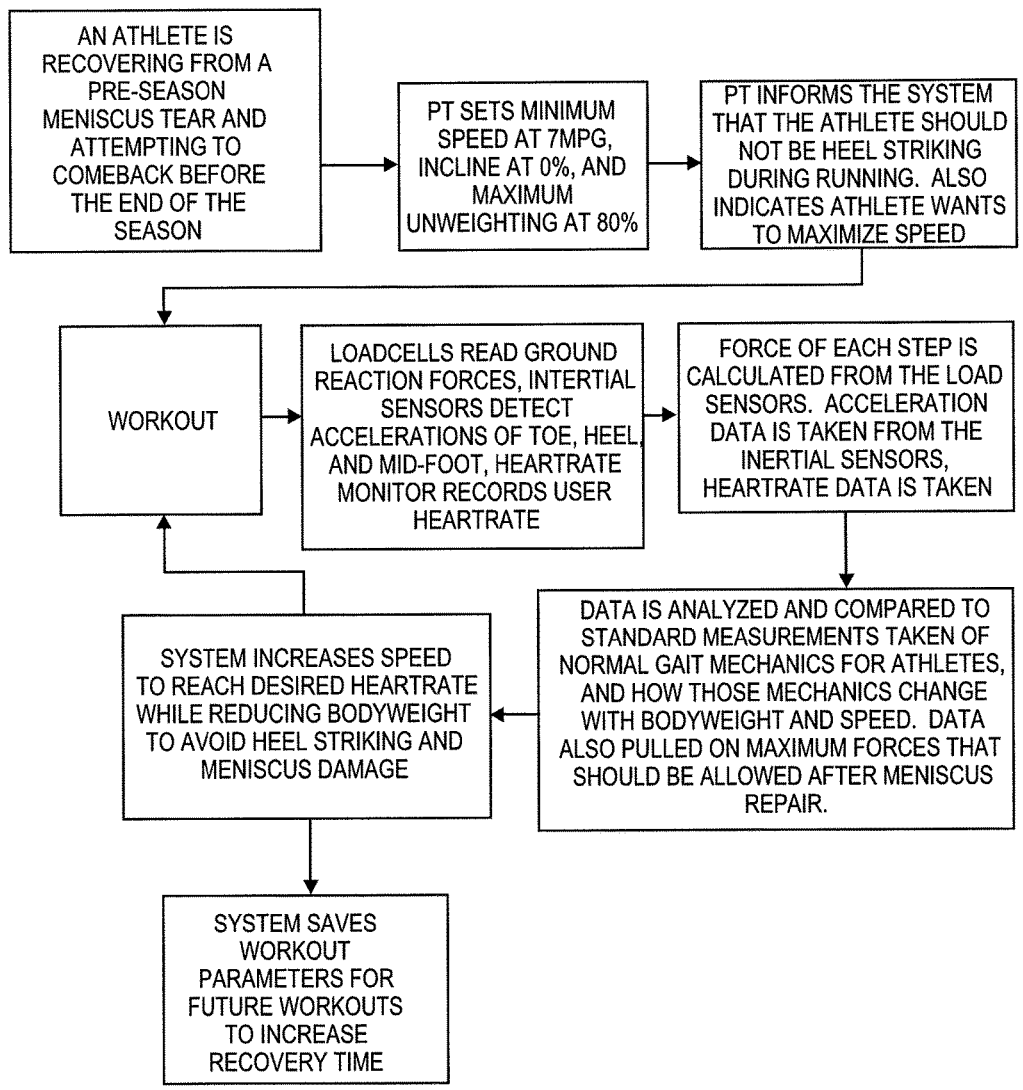
FIG. 18 is a specific patient example for the use of the system in FIG. 15 using the methods and work flow of FIGS. 16 and 17.

FIGS. 16 and 17 provide examples of a work flow (FIG. 17) and data stream/synthesis (FIG. 16) for the exemplary system. FIG. 18 provides one specific example of how a system may work is that the therapist sets the system to improve the pronation of the foot during the push-off phase of walking. The patient in this example would likely use a category 1 system as described in the '124 application. The therapist also sets the maximum speed at 2 mph, so as not to cause the patient to start running. The system will then go through a diagnostic process where it changes weight, incline, and effective bodyweight while providing audible, visual, tactile or other feedback to the patient regarding the parameter to be modified, determining which combination of settings enables the patient to achieve the best pronation of the foot. As the workout goes along and the patient works on improving their pronation, the unit can incrementally increase the effective bodyweight as a means to eventually train the patient to pronate their foot at full bodyweight. If the system starts to detect the user is having trouble pronating, it can also either slow the treadmill or unweight the patient to a greater degree to give the user more time to pronate the foot or reduce load on the foot to enable better pronation. At the end of the workout, the therapist would receive a report of how the user progressed and a suggestion for where the next workout should begin.

Figure 19:
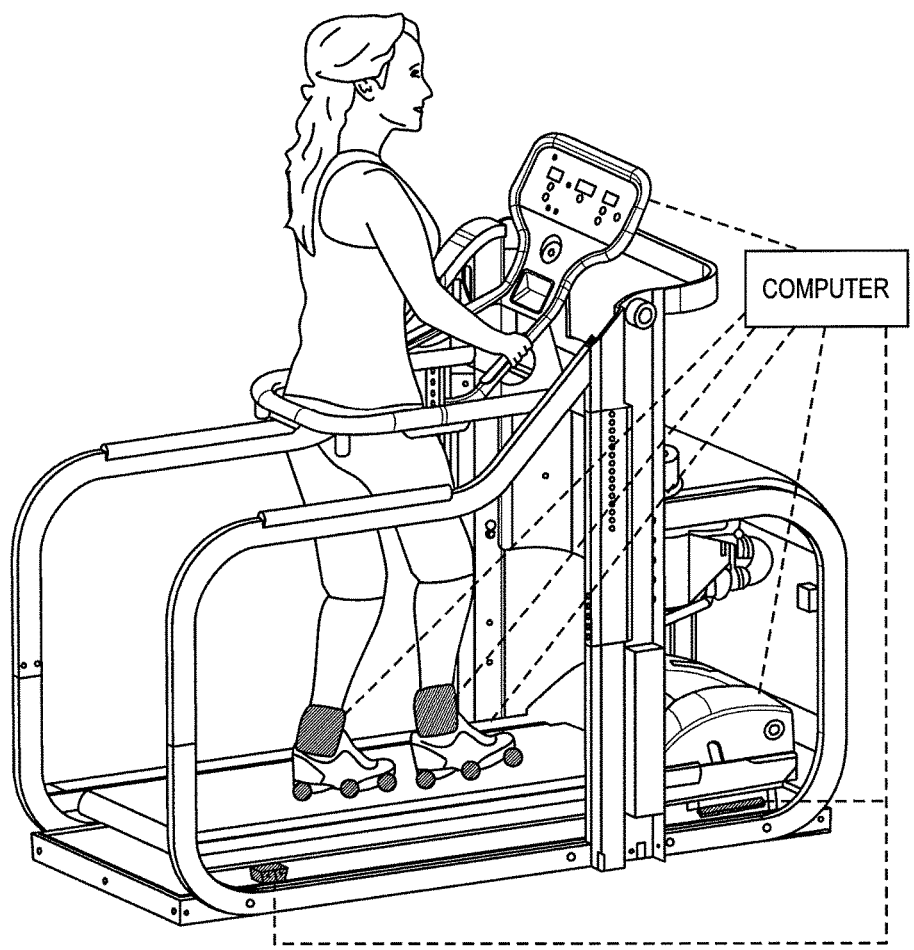
FIG. 19 is an isometric view of a differential air pressure training system have additional gait data measurement devices.

FIG. 19 illustrates still another exemplary system using gait analysis tools, DAP Technology, and biofeedback to train and/or improve gait. In this view, the pressure bag that normally covers the frame and defines the pressure chamber is removed to permit the interior details of the pressure chamber and the instruments contained therein to be observed. With regard to the training technique of FIG. 19, an additional feature is the continuous recording of the electrical activity of the muscles in the form of electromyograms (EMGs). These are real-time recordings of the electrical activity of the muscles measured with surface electrodes, or, optionally, with fine wire electrodes, or with a mix of electrode types.

Figure 20:
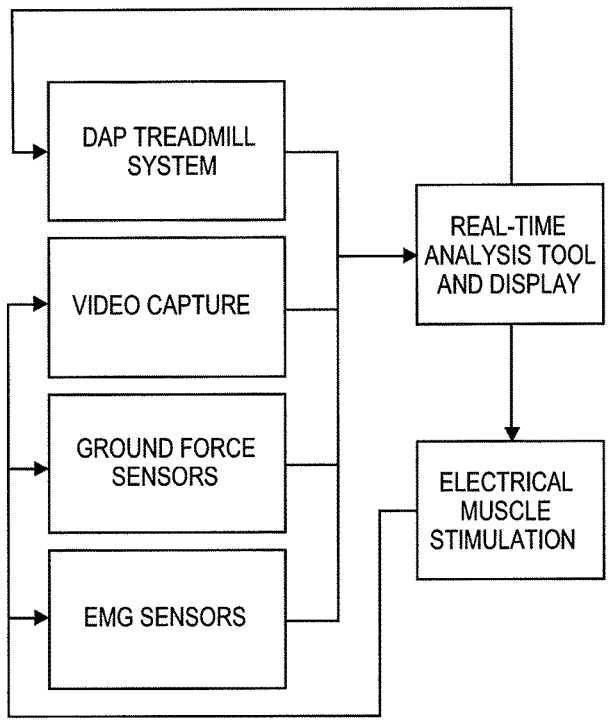
FIGS. 20 and 21 are information collection and work flow examples for the use of the system in FIG. 19.
Figure 21:
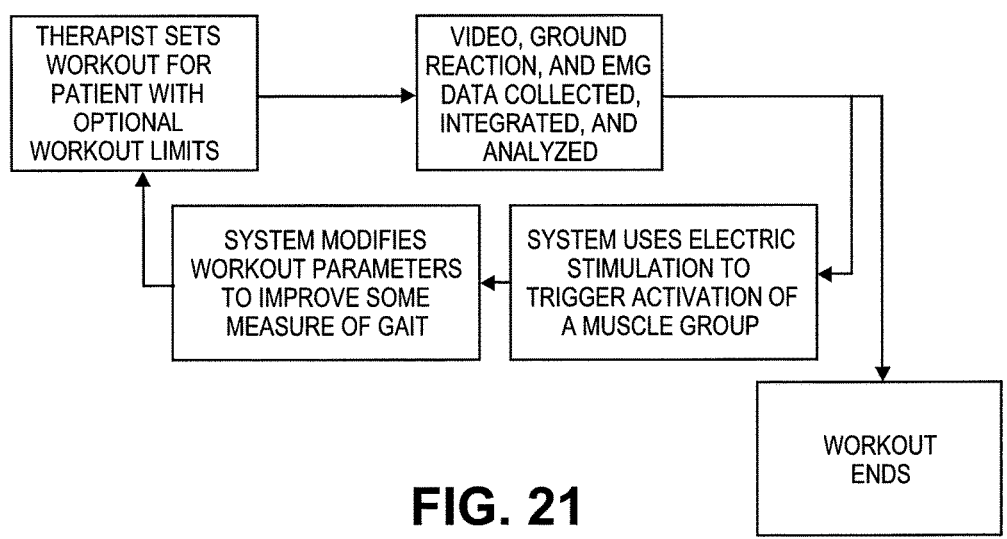
Figure 22:
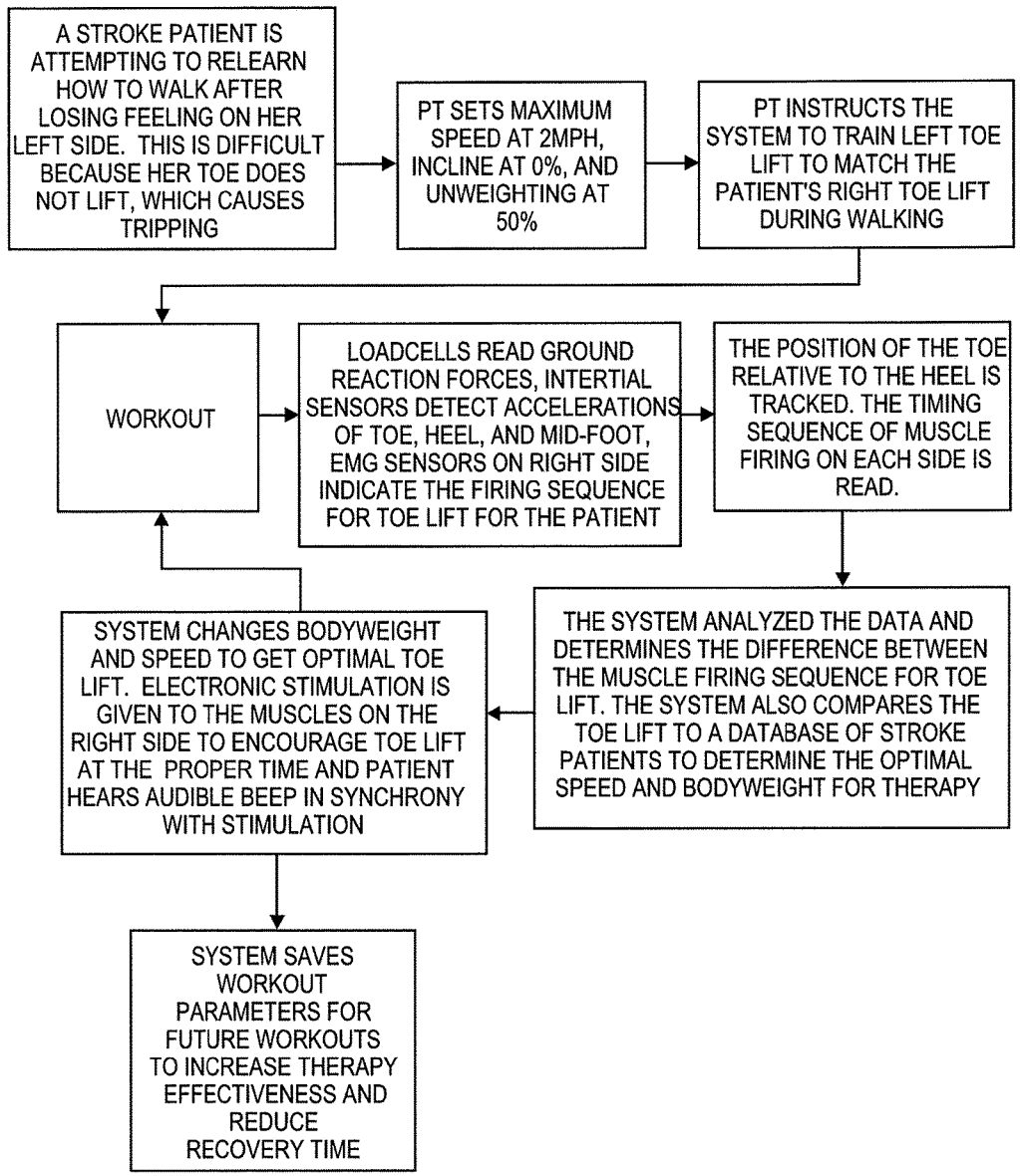
FIG. 22 is specific patient example for the use of the system in FIG. 19 using the methods and work flow of FIGS. 20 and 21.

FIGS. 20 and 21 provide examples of a work flow (FIG. 21) and data stream/synthesis (FIG. 20) for the exemplary system. FIG. 22 provides a specific example for a patient undergoing such therapy. The patient in this example would likely use a category 3 system as described in the '124 application. In one specific aspect, some patients undergoing gait correction therapies may have suffered an injury that impedes the normal biological feedback loops that exist in the body. For example, a stroke patient may no longer be able to feel pressure in their right leg as sensitively as they feel pressure in their left leg. This will cause an asymmetry in gait that needs to be corrected. Even with gait analysis and automatic workout adjustments, the patient may still have problems achieving regular gait due to the damage to the biological feedback loop of the patient. In current therapies, the therapist manually adjusts the position of the patient's legs. In a differential air pressure environment, access to the patient's lower body can prove difficult. By adding some other form of biological feedback being controlled by the system, a patient may be able to more rapidly achieve proper gait mechanics, without the necessity of a therapist manually manipulating the legs.

In various alternative embodiments, there may be used one or a variety of types of biofeedback integrated into a system with gait measurement, analysis, and DAP based upon the specific therapy needs of a specific patient or class of patient. For purposes of illustration, exemplary types of biofeedback may include indicators to give the patient a sensation that triggers the patient to act such as an audible alarm when the patient needs to lift their leg, an electronic stimulation sequence that starts a muscle firing sequence to extend the foot, a visual cue and the like. One additional aspect of the embodiment of FIG. 19 is the provision for the full stimulation of designated and associated action groups to help with training of a targeting muscle group. The full stimulation may be caused by electronic stimulation controlling one or more muscle groups as well as mechanical apparatuses that work to augment the function of one or more muscle groups. In one example, the targeted stimulation area is a muscle group. In another, the targeted muscle group is a tendon group or area. For example, when the leg is being raised, flexor and associated tendons in the lower hamstring area on the back of the leg are optionally subject to vibration or another type of full stimulation. This is thought to strengthen the desired nerve pathways to allow the patient to develop toward over ground locomotion. Therapeutic stimulators meant to provide sensation may provide electrical stimulation or may be vibrator or other tactile stimulators or other sensory stimulators triggered in synchrony with the therapy, as needed.

EXAMPLES

In one example, a Differential Air Pressure System having gait correction capabilities integrated with a prosthesis or other proprioceptive feedback or training device. In this specific example, the integration of a differential air pressure system with gait capabilities as described above with machine control capabilities, enables feedback or training using muscle memory motion via an assistance device. Additionally or alternatively, there may be modifications to the control system depending upon the control requirements of the type of motion assist device incorporated into the DAP system.

In still another example related to a sensor of the type worn by a patient, the patient may wear shoes having integrated instrumentation such as, for example, motion sensors, inertial sensors, force sensors and the like. The shoe may store the data collected from the onboard sensors onboard for later incorporation and synchronization with other system collected data. Additionally or alternatively, the shoe may include transmission capabilities to send data from the shoe to a suitable receiver on the system. In this way, data from the shoe(s) used by the patient are included into the simultaneously collected data stream as discussed above. In still another embodiment, the shoe sensor is used to record patient activity while outside of the differential air pressure training system described herein. Data may also be collected from sensors worn outside of the DAP training and integrated with the data collected when using the DAP system with integrated gait capabilities. This would for example enable the system to determine differences in gait pattern evident while training at partial body weight with the sensor data indicating gait parameters in full body weight locomotion. Still further there is provided access for collection of other exercises conducted in support of the patient training. For example, a patient conducting strength training in addition to DAP gait training may have that training data downloaded or entered along with the DAP gait training data in order to have a comprehensive data set collected in the DAP gait system that reflects the patient's entire training and therapy effort. For example, a patient with a stroke causing impairment in one leg, may have strength training data in that leg correlated by the system with gait changes to determine which strength training processes are helping to improve gait and to reinforce which specific muscle groups need further therapy for flexibility, strength or other parameters in order to achieve desired gait improvement.

In one specific example, there is a shoe based sensor system that collects and stores or collects and transmits data on various pressure points to provide gait instruction while using a system described herein or performing one of the illustrative methods of therapy. The DAP gait system integrates with the shoe based data collection system in a feedback loop to unweight a patient to achieve desired gait, and then capture data or, optionally, provide biofeedback based upon sensor inputs when they are off the treadmill in normal activity. In this way, the integrated DAP gait training system becomes part of the treatment modality to use unweighting therapy and biomechanics training as part of the feedback loop to accelerate biomechanics modification.

In still another specific example, patient uses a differential air pressure system with gait training capabilities to unweight and retrain while integrating foot sensor data to achieve desired patterns. The patient practices during several thirty minute sessions at slowly progressing reloading while maintaining the desired pattern. When the patient can achieve the desired sensor and biomechanics pattern at 90% of body weight, the patient is provided shoes with the sensors to take home and use regularly recording the data and feeding back real time data to a mobile device such as a cell phone, personal data assistant (PDA) or smart phone. The data tracking shows how closely the patient is adhering to the desired walking mechanics achieved in the DAP environment and what deviations are monitored. The next session on the DAP gait training system, the gait training protocol uses that data to determine unweighting and a training program that specifically helps correct the poor mechanics tracked in the full weightbearing environment. When proper mechanics are achieved in the unweighting environment, another series of 30 minute practice sessions using those mechanics while unweighted with biofeedback to maintain proper gait is provided to help the patient relearn proper gait mechanics. This pattern is repeated several times until the patient reliably and repeatably adopts the new gait pattern and maintains that pattern in full gravity walking.

Figure 23:
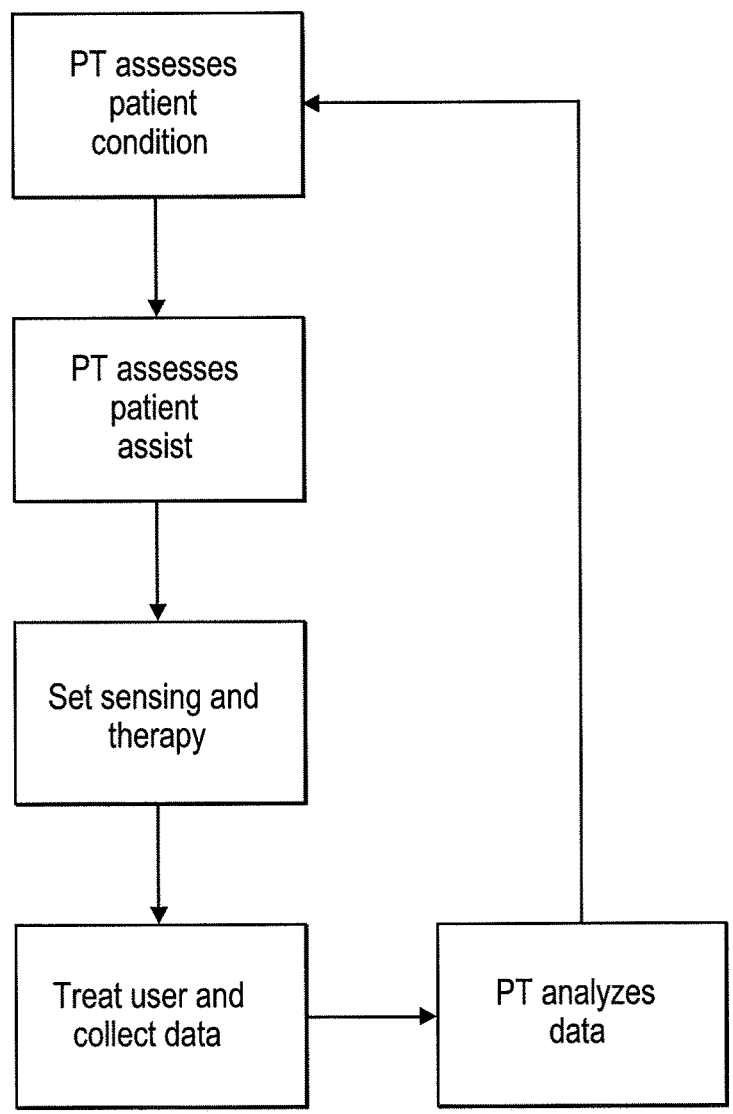
FIG. 23 is another illustrative therapy method of using differential air pressure assisted training using gait measurements and physical therapist analysis to adapt therapy.
Figure 24:
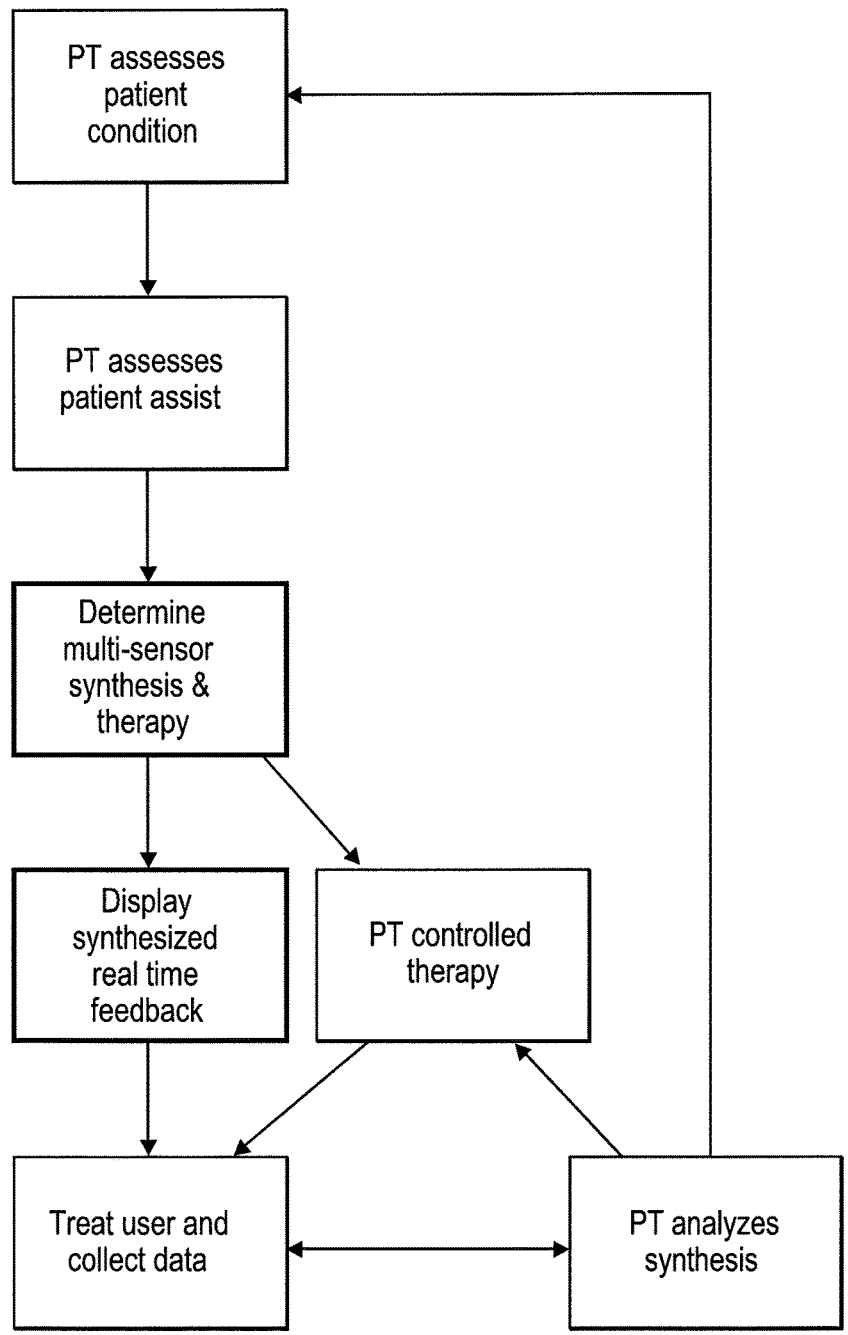
FIG. 24 is another illustrative therapy method of using differential air pressure assisted training where therapists determine appropriate multi-sensor synthesis and therapy, with display of synthesized real time feedback, plus adjustments to therapy that are controlled by the physical therapist.
Figure 25:
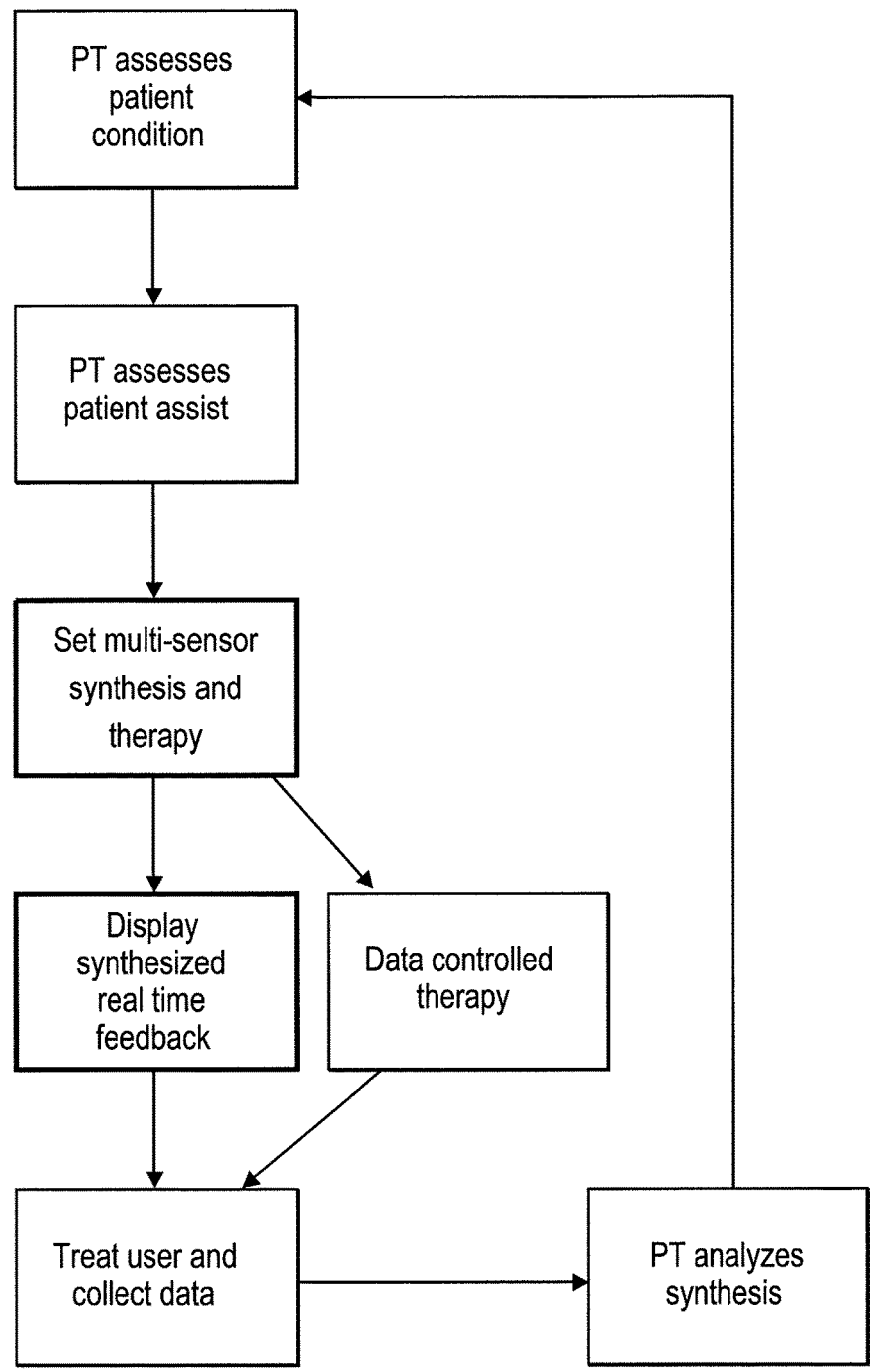
FIG. 25 is another illustrative therapy method of using differential air pressure assisted training where therapists determine appropriate multi-sensor synthesis and therapy, displaying synthesized real time feedback that is data controlled.

FIGS. 23, 24, and 25 are flow charts of additional patient training work flows using the DAP and gait systems described herein.

The various embodiments of an integrated differential air pressure and gait training described herein also includes a computer controller in communication with the various system inputs (see, e.g., FIGS. 2, 5, 9, 16, and 20) as well as other components for the control and monitoring of the therapy system. In some embodiments, the system receives inputs from data collected by GaitBox used with the system. A keyboard and a monitor attached to the system or available during use enables the user or a trainer/therapist to input selected differential air pressure, calibration, kinematic parameters, gait parameters, dynamic stepping parameters and other parameters depending upon patient therapy objectives and system configurations into the computer-based control and performance monitor system. The term user, here, covers the patient and/or a therapist and/or a physician and/or an assistant. A user interface to the system is implemented by a keyboard/monitor setup or GUI screen or touch pad or wireless controller attached to or in communication with the system control computer. In one aspect, the input device is easily reachable by the patient, as long as the patient has enough use of upper limbs. It enables the user (therapist or patient) to input selected kinematic and dynamic stepping parameters, treadmill speed, differential air pressure and other system specific parameters into the control and monitor system. A condensed stepping performance can also be viewed on this monitor interface in real time, based on preselected performance parameters (see e.g., the display in FIG. 3 or FIG. 8). It is to be appreciated that display in that configuration or in others may be modified to include an externally located digital monitor system displays the patient's gait and/or stepping performance in selected details in real time. In one aspect, the display is triggered for collection or display based on other parameters such as in the heel strike example above for recording a video data stream of knee bend.

In addition, the system control computer includes the components and sub-systems used for a data recording system that enables the storage of all training related and time based and time coordinated data, including electromyogram (EMG) signals among others as illustrated and described above in FIGS. 2, 5, 9, 16, and 20. In addition or optionally, the system receiver inputs from data collected by or provided from a GaitBox used with the system. This collected data may be used in real time or near real time during a therapy session. In still further examples, the collected data may be stored for off-line diagnostic analysis, therapy adjustment and planning with other patients of similar type. The architecture of the data recording part of the system enables the storage of all training related and time based and time coordinated data, including electromyogram (EMG), torque and position signals, for off-line diagnostic analysis of patient motion, dependencies and strengths, in order to provide a comparison to expected patterns of nondisabled subjects. The system will be capable of adjusting or correcting for measured abnormalities in the patient's motion. In still further alternatives, the data collected may be normalized to a common data collection standard for differential air pressure treatment systems to remove variations in specific equipment, components, measuring devices and the like. The normalization or standardization of data collection enables the data collected from one patient to be used to guide the therapy of another patient by showing performance parameters and system configurations.

In one aspect, it is to be appreciated that the integrated DAP system with gait measurement may be operated to use differential pressure assistance to selectively and controllably adjust the mechanical load acting on the patient while optimizing the work or therapy performed by the patient to provide effective stepping and standing during therapy along with measurable and repeatable data collection, synthesis feedback into specific therapy regimes and protocols.

In still another aspect, the systems and method of gait training described herein (optionally including the use of a GaitBox for data collection) provide a true user controlled gait training environment. The integrated DAP and gait measurement systems of FIGS. 3 and 8, for example, provide the user or trainer with feedback that permits the immediate connection of alteration of system parameters or gait change to feedback. The ability of a user or trainer to see immediately the outcome of the latest change to system settings or gait modification as improving, worsening or have no impact is an important link in the therapy chain as yet unattained by conventional training systems. The freedom of range of motion provided by the DAP training system minimizes or reduces the impact of patient off-loading from adverse gait impact. In other words, other patient assist devices such as harness or suspension systems tend to alter gait artificially rather than permitting the uninhibited range of motion afforded in a DAP environment.

The GaitBox provides accurate, real-time measurement of basic gait parameters on any treadmill.

The basic gait parameters are: Speed (distance divided by time); Cadence (number of steps per minute); Left/Right Stride Length (distance between successive impacts of same foot, e.g. left-foot-impact to left-foot-impact); and Left/Right Stride Time (time between successive impacts of same foot). Other additional gait parameters include, by way of example and not limitation, foot placement phase asymmetry (right to left step time compared with left to right step time) and stride time jitter (variation in timing between subsequent footfalls on the same or opposite sides).

Figure 32:
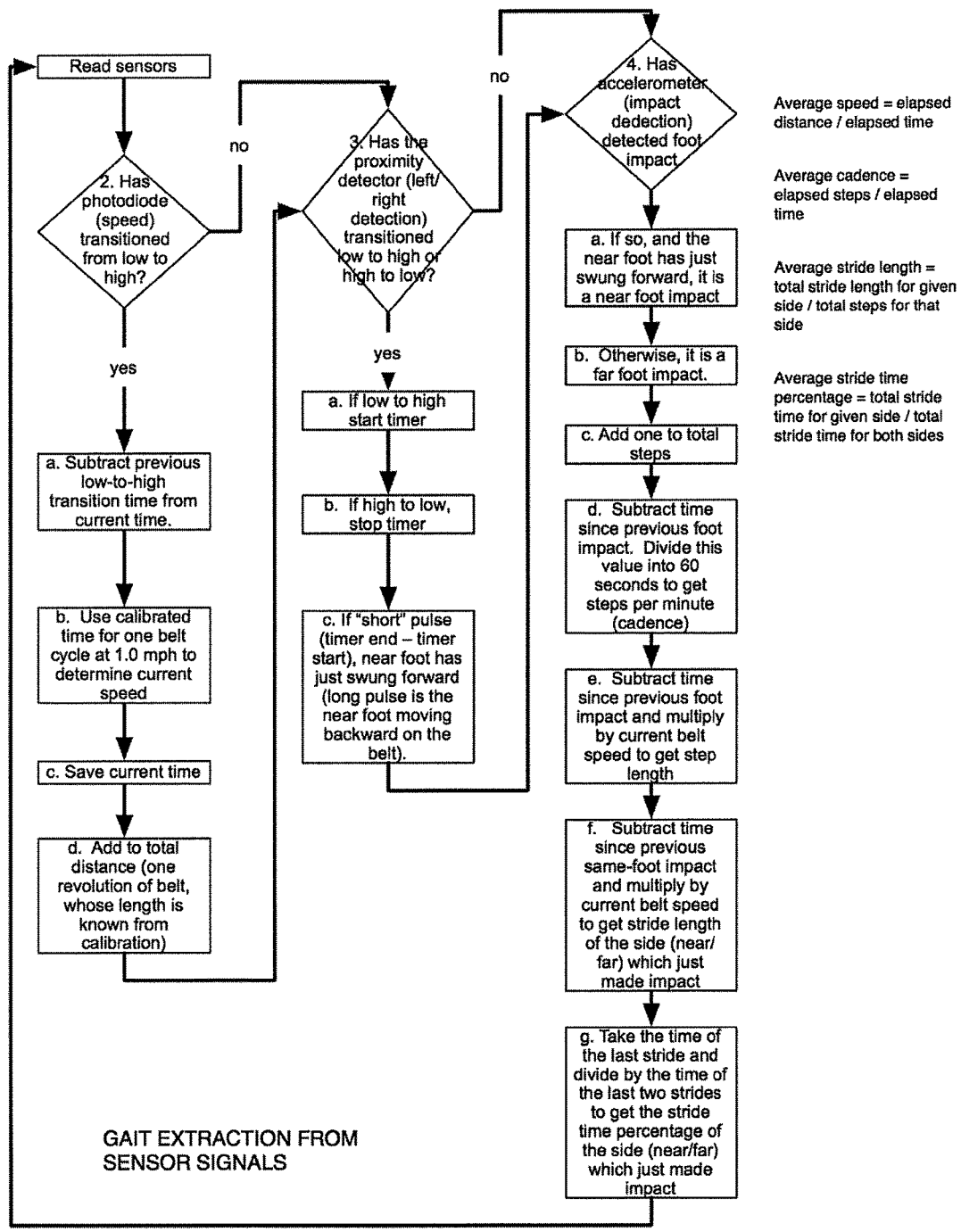
FIG. 32 is a flow chart of one a technique for biometric factor calculations.

FIG. 32 illustrates a method of calculating a variety of factors.

In one aspect, to calculate these values when someone is walking or running on a treadmill requires:
An accurate (microsecond resolution) clock
The speed of the tread belt
The time of foot impact, and
Which foot (left/right) impacted the tread deck In one embodiment, the GaitBox obtains these measurements in the following ways:

Accurate clock—the various sensors are attached to a microprocessor which has a regular clock interrupt with 4 microsecond resolution.

Tread Belt Speed—an infrared emitter/detector pair (sensor) is positioned over the treadmill belt so that reflectivity of the belt surface under the sensor can be measured. A strip of reflective material of a precise, known length is applied to the treadmill belt, so that reflectivity of the belt surface changes dramatically while the strip is under the sensor. The duration of the period of high reflectivity (as measured by the microprocessor clock) gives the treadmill speed. For example, if a one-foot strip of reflective material takes one second to pass under the sensor, the speed of the tread belt is 1 foot/second, or approximately 0.68 miles per hour. At higher speeds, once the system has been calibrated to the known length marker, front to front or rear to rear edge detection can also be used for greater accuracy for a given sampling rate.

Time of foot impact—an accelerometer is attached to the treadmill frame. When a foot impacts the tread mill deck (which is supported by the treadmill frame, perhaps with cushioning), the resulting acceleration of the deck is transmitted to the frame and sensed by the accelerometer and "stamped" with the elapsed time in microseconds as measured by the microprocessor clock. An acoustic sensor can also be used to detect for impacts. Alternatively, a different marker of stride periodicity can be used, such as when each leg passes in front of the proximity sensor or sensors.

Which foot—an infrared proximeter is mounted so that its beam (and hence area of detection) is directed perpendicular to the direction of belt travel. The "near foot" (closest to the proximeter) interrupts the beam twice: once briefly, during the swing forward (towards impact) and again when the foot is planted on the treadmill, moving backwards. When swing forward is detected, the next impact will be for the "near foot" (left or right depends on the side to which the GaitBox is mounted).

FIG. 30A is a perspective view of a GaitBox. The GaitBox is an enclosure with a pair of sensor (S1, S2) positioned in an appropriate location and aspect on the enclosure to obtain information for user calculations as described above. Shown in phantom on the top of the enclosure is an optional display.

FIG. 30B is an illustration of the functional components of a representative GaitBox. The sensors (S1, S2) may be any sensor suited to obtaining the user parameters described herein. Exemplary sensors include IR sensor, optical mouse style laser sensors, proximity sensors, light or other sensors suited for use in the GaitBox operating environment. The processor includes the computer readable instructions to receive and process the output from the sensors (S1, S2). The process may provide the outputs listed or other outputs as desired for any of the above-described Gait analysis or system implementations. As illustrated, the processor may provide an output to a display that is on the GaitBox (see FIG. 30A) or in communication with the GaitBox. The display may be separate from the GaitBox and any associated exercise equipment or Gait processing system or it may be integrated into these other systems. The GaitBox also includes one or more of typical communication modes based on the desired operations or use of the GaitBox outputs.

It is to be appreciated that one or more of the GaitBox characteristics, functions or capabilities may be used to provide inputs/outputs or other information to enhance the operations of the various Gait techniques as shown and described herein.

Visual Display

The basic visual display of the GaitBox may be on the GaitBox (FIG. 30A) or provided as an output to a dedicated device or to a display that is part of the exercise equipment or Gait system used in cooperation with GaitBox. In general, the visual display presents the following information:
  Elapsed Time (updated every second)
  Elapsed Distance (updated every second)
  Elapsed Steps (updated every step)
  Average values for
    Speed (total distance/total time—updated once a second)
    Cadence (total steps/total time—updated every step)
    Left/Right Stride Length (total length of strides on given side/total time—updated after each stride)
    Left/Right Stride Time Percentage (total time of strides on given side/total time—updated after every stride)
  Instantaneous values for
    Speed (current speed reading)
    Cadence (based on the duration of the last step—updated after every stride)
    Left/Right Stride Length (length of last stride—updated after every stride)
    Left/Right Stride Time Percentage (duration of stride on given side/duration of last two strides—updated after every stride)

As mentioned above, the visual display can be presented via native software running on a PC, a tablet, or a smart phone, i.e. a software application designed to run on one or more of these platforms). Although the microprocessor in the GaitBox itself may do some processing of the raw sensor date (e.g. noise filtering or error correction), the actual data display is performed by the software application running on the display device. We will refer to this as the "GaitBox application" (as opposed to the GaitBox hardware, consisting of the sensors and microprocessor).

As shown in FIG. 30B, the Gaitbox will communicate with the display device wirelessly via Bluetooth or Wi-Fi, although other implementations could use a wired connection such as Ethernet or RS-232.

Video

In an alternative embodiments or in addition, the GaitBox system incorporates one or more video cameras, which can communicate with the processor and/or as well as visual display in either a wired or wireless configuration. In one aspect, the visual display will show the video in real time. In some configurations, the video may appear on a separate "page" which can be selected by the user, or alongside other information on the primary screen. If multiple cameras are available, the GaitBox application provides for selection of the camera to be displayed. In some embodiments, a GaitBox application provides for simultaneous display of multiple camera views.

Visual Feedback

In some aspects, the computer readable instructions in the application which manage the visual display provide for drawing edits such as lines and shapes (e.g. rectangles or circles) or other visual indicia on top of the video. These user provided drawings may be implemented using a touch screen, for example.

In addition to the basic gait parameters, the application which manages the visual display may provide graphic feedback as to the symmetry of gait. For example, two bars (representing left/right stride length) might appear on the display, and the user instructed to make the two bars equal in length (and of a specific height, i.e. stride length).

Reporting

The GaitBox application includes computer readable instructions to generate a summary report (total time, total distance, total steps, average speed, average cadence, and statistical measures of left/right stride length and time percentage (min/max/mean/median/standard deviation) or any other collected parameter, calculated parameter in any combination or as specified by a user. In addition, the report may be preserved in some fashion either on or off the display system (e.g. printing, stored as a file, or e-mailed).

User Identification

Some versions of the GaitBox application will allow the user to identify themselves. For example, on a smartphone the Gaitbox application might be used to scan the QR code from a membership card. A PC-based implementation of the GaitBox application might recognize an RFID chip or incorporate a fingerprint scanner. Once identified, the gait information collected by the GaitBox application (including video, in some implementations) would be associated with that user.

Data Storage

Some implementations of the GaitBox application will allow the results of a session to be saved locally. Some implementations will allow the information to be saved on a server on the Internet. Data storage may be performed using any of the communication modes available (see FIG. 30B) or via USB, firewire or other physical data port provided on a GaitBox.

Web Access

If GaitBox session data is saved to a server on the Internet, a Web-based application will make that information available via a browser. If information is associated with a particular user, they will have the ability to see only the information from their own sessions.

While the various Gait techniques and systems and the GaitBox are shown in use and configured for providing therapy utilizing DAP systems, the various embodiments of the present inventions are not so limited. The gait methods and systems described herein, particularly for the GaitBox, may be adapted and configured for use with a treadmill with (as described) or without a DAP or other assisted use device.

In addition to the above described, techniques, other variations of implementing the system are possible. In one example, at low walking speeds, detecting a foot strike with an accelerometer mounted to the treadmill deck is challenging, due to the amount of background vibration induced by the treadmill motor itself. An alternate embodiment is to use an acoustic microphone alone or in conjunction with any of the above described aspects to detect foot strikes. In still another alternative embodiment, the detection of foot strikes is neglected altogether and instead leg proximity sensors are employed to measure the intervals between successive passages of the legs in front of the sensors.

To capture more complete workout data, the present invention can also capture user's heart rate and treadmill incline through wireless heart rate monitoring sensors and gyroscopic or accelerometer sensors In situations where patients progress through a continuum of care, from immobile, to partially mobile, to fully mobile, gait data generated by the current invention can be connected and compared with data from devices aimed at other segments of the care continuum. An example might be gait data collected from a Tibion bionic leg matched against data collected from the present invention, compared to gait data collected from full mobility measurement system such as those produced by Optogait or Zebris. Doing so allows showing efficacy of treatment over time, beyond the range of any single system.

Figure 31A:
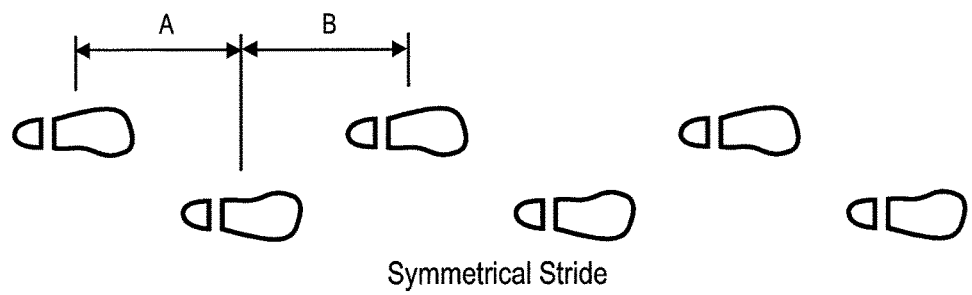
FIGS. 31A, 31B and 31C illustrate normal and exemplary gait abnormality foot fall patterns.
Figure 31B:
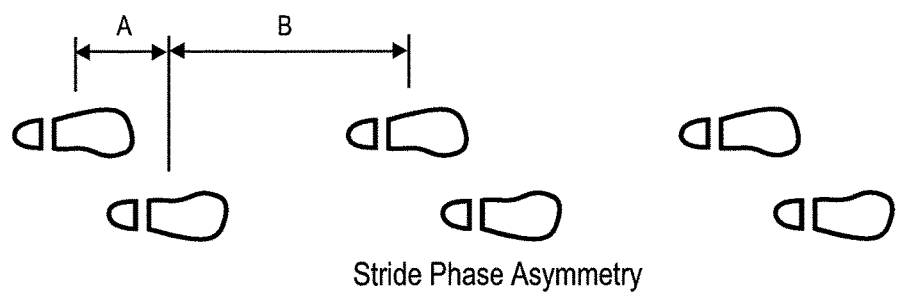
Figure 31C:
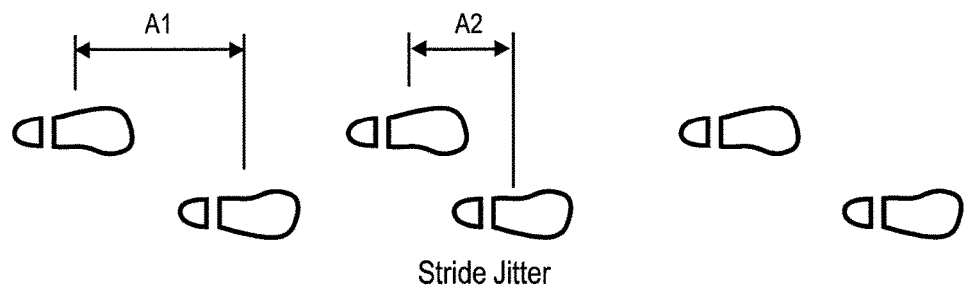

The current invention enables the measurement of gait asymmetry through the use of leg proximity sensor mounted on either side of the treadmill by reference to FIGS. 31A-31C. FIG. 31A is a normal symmetrical stride. FIGS. 31B and 31C illustrate two kinds of gait abnormality, phase asymmetry (FIG. 32B) and stride jitter (FIG. 31C). In FIG. 31B A is compared to B. In FIG. 32C, A1 is compared to A2.

In still further aspects, the Gait methods and systems described herein, in particular the GaitBox embodiments, may be used in conjunction with other unweighting devices or systems. Exemplary non-DAP based unweighting systems are described in, for example, co-pending commonly owned provisional patent applications: "SUPPORT FRAME AND RELATED UNWEIGHTING SYSTEM," filed Mar. 14, 2013, application No. 61/784,387, "CURVED ARCH UNWEIGHTING SYSTEMS," application No. 61/772,964, filed Mar. 5, 2013, "UNWEIGHTING ARCH SYSTEMS," application No. 61/773,019, filed Mar. 5, 2013, "MONOCOLUMN UNWEIGHTING SYSTEMS," application No. 61/773,037, filed Mar. 5, 2013, and "CANTILEVERED UNWEIGHTING SYSTEMS," filed Mar. 14, 2013, application No. 61/784,510, each of which are incorporated by reference its entirety.

In a further exemplary implementation of the above described systems, there may also be available to a user a progression of personal assistance, unweighted training and rehabilitative systems along with other non-assistive or conventional exercise systems. This variety of training systems may be considered a continuum of care. An individual may be training to recover from a stroke or surgery. Such an individual may not be able to move without assistance. As such, one of the assistive devices described herein would be used as the starting point for this person's training or rehabilitation program. In one aspect, the user may be provided with an assistive device that in this context refers to a device that may include an actuator or other form of imparting locomotion to the user's limb or frame to assist the user in the biomechanics of walking. In one aspect, there may be one or more actuators coupled to the person's limbs or about one or more joints to aid in moving the person's limbs to provide assisted mobility training. Next, after some sessions and improvements, the person may progress to one of the various unweighting systems or other assistive training systems described herein. After a progression through the stages of assistive training, the person may progress to the use of unassisted training or exercise equipment. In general this continuum of care from fully assisted (alone or in combination with unweighting training) progresses to unweighting types of training. The user may then progress to lesser amounts of unweighting (i.e., the unweighting system provides less and less assistance) as the user gets stronger and more able to accomplish gait and mobility independently. Until the user reaches the use unassisted exercise and independence of gait and other biomechanical training and rehabilitation.

The systems described herein may also be configured to accommodate a user's progress through the above mentioned stages or continuum of care from assistive locomotion devices or systems, to unweighting systems to lesser degrees of unweighting systems to the use of conventional exercise equipment and training systems. In the exemplary descriptions of the implementation of these integrated training systems, the term "training device" is intended to include any of the herein described training systems including assisted locomotion devices or systems or actuator based limb mounted components; non-DAP unweighting systems; DAP unweighting systems or conventional training systems such as treadmills, stationary bikes, elliptical trainers, stair climbers and the like.

Referring again to FIG. 5, the system downloads a treatment or workout program to the appropriate assisted, unweighting or other training device. Either the training system or the treatment management and scheduling system may send an approval request to a medical professional or to an insurance provider for approval. For example, a networked training device could be pre-set for a workout session based on knowledge of who will be using the machine during that session. A physical therapist could adjust the program locally as required, either prior to or during the session. The system will allow for review and modification of a recommended user program by the associated physical therapist or trainer. For example, in some embodiments, the system allows a therapist to create or modify pre-programmed workout sessions and attach these to an appointment scheduled by the user, overriding any system-generated workout session. In some embodiments, the training device or systems have editing capabilities on a display/control unit associated with the treadmill, or on a mobile device by means of an "app." In some cases the display or control unit is removable.

Once the treatment is set, the user gets into the training device or system and performs a treatment or workout according to the suggested treatment protocol provided either by the training device or system, the treatment management and scheduling system, the physical therapist, or a combination of these.

In some embodiments, prior to starting the treatment, the user is identified by the DAP system as the proper user for the specific treatment. For example, the training device or system may be capable of identifying the individual user, based on some unique ID which is presented to the machine prior to use. The system will know the age, sex, and medical diagnoses (if applicable) of each user. In some embodiments, the system may require that a user who has scheduled time on a machine to identify themselves to the machine (via keypad, RFID, bar/QR code, magnetic card swipe, biometrics, or other identification technology) at the beginning of their scheduled session. This provides confirmation that the user kept the scheduled appointment, ensures that any treatment protocol sent to the machine is used by the intended user, and allows performance data to be attached to that user's treatment history. Where a patient does not have an identification means, the user can create a profile. The training device or system may maintain a profile of each user. In general, users will identify themselves prior to using the system. In some embodiments, a "guest" identification acts as a catch-all for users without a profile. The system will track utilization by individual users and can report on utilization statistics and workout parameters to the healthcare practitioner for medical evaluation, to the user for personal medical and health records and monitoring, and to third parties such as insurance providers or reimbursement agencies for medical reimbursement to the clinic or healthcare practitioner or for compliance verification of activities by the patient associated with medical insurance or wellness program monitoring.

Advantageously, in some embodiments, a patient identification means can help monitor (and encourage) a patient's compliance with a treatment program. The patient's identification means such as an access card may be read by a medical professional during scheduled checkups to monitor the patient's progress. Monitoring progress may also be used to track, monitor, adjust or improve upon a user's progression along the continuum of care as described above.

Once the user has completed his session, the user can provide feedback to the training device or system in any number of ways. For example, the training device or system can receive and store information on the user's satisfaction with the treatment, overall mood, level of pain, etc. In some embodiments, the training device or system is capable of recording a broad range of information about user performance, including but not limited to duration, speed, incline, percentage body weight, heart rate, and gait factors. Moreover, the training device or system can receive and store information provided by a medical professional observing the user's treatment on the training device or system. For example, a physical therapist may rate the user's progress and/or provide notes on the user's treatment, or progression from one assistive device or technique to the next along the continuum of care described above. Any of this information can be directly entered into the device or training system either by a computer terminal interface connected to the device or system or through a receiving means directly connected to the device or training system. For example a touch pad monitor may be connected to the device or system to receive input.

The device or training system may also be configured to send information to another device such as a printer or computer. The information can be sent via email to a doctor, insurance company, or a patient file. In other embodiments, the information can be printed and added to a physical file at the facility. Additionally, the information may be sent to the treatment management and scheduling system to be stored in the database for archival and retrieval purposes. For example, the training device or system may be capable of transmitting that information to a central information processing system.

In some embodiments, information is sent to a doctor or insurance company if the treatment protocol indicates that more sessions are required and the user does not have a prescription or insurance coverage for the remaining suggested sessions. In some embodiments, a predictive algorithm is used to evaluate whether a suggested treatment protocol generated by the training device or system or the treatment management and scheduling system is consistent with the prescribed treatment by a medical professional. In one aspect, the system will also predict or recommend the progression of a user from one type of assisted training device or system to another based on user performance, goals, historical data or one or more factors provided by a predictive training algorithm. If, for example, the predictive algorithm shows that the number of covered sessions remaining is less than the number of treatments predicted to achieve the desired outcome, the system (DAP, non-DAP, training device or system or treatment management and scheduling) will generate a reminder to the facility/therapist that re-authorization is required. The system may also generate the required documentation needed for re-authorization.

In some embodiments, to determine proper scheduling of the appropriate training device or system, the treatment management and scheduling system evaluates criteria besides the machine being used, such as specific therapist or skill set, whether the patient needs assistance in entering or using the machine (including need for lift access or a particular personal training device or locomotion system or gait monitoring system), video recording systems, gait analysis capabilities, insurance qualification and provider network, and transportation to/from the appointment.

In some embodiments, the system will use data from gait analysis, user performance, user experience, etc. to drive scheduling. For example, the treatment management and scheduling system may receive and gather a user's information after the first treatment. Based on that information, the treatment management and scheduling system can provide the user with additional sessions or a series of sessions for continued treatment based on the first treatment and the end goal. In other embodiments, the treatment management and scheduling system continuously assesses the user's performance and information after each session to determine whether to modify treatment parameters or scheduling. For example, a user reports that they experienced pain during the appointment, the system may suggest delaying the next appointment, to allow for more recovery time or may recommend a greater degree of unweighting, or different unweighting system or technique at the next session. If the machine senses gait asymmetry that may be associated with muscle strength, the system may recommend possible strength or flexibility rehab therapies as part of the PT evaluation and possible treatment considerations and the system could monitor compliance with specific recommended activities if such activities are performed on machines connected to the system or if the patient is wearing sensors that enable data capture of such activity when not on connected machines.

In further embodiments, the treatment management and scheduling systems allow a sequence of appointments to be scheduled, based on either a number (e.g. 10 appointments) or a desired outcome (e.g. walking at 3% incline at 2 mph at 95% of body weight). Rather than schedule a single appointment as described, multiple appointments can be scheduled by the user according to desired number of appointments or treatment protocol. The system can monitor patient compliance with the treatment schedule and can monitor patient progress toward the desired outcomes. If necessary, the system can communicate recommended or possible modification to the treatment sessions required. Such communications could be provided to the healthcare practitioner, to the patient, to the insurance provider or to other parties with associated data and rationale based on patient-specific or population data metrics.

In some embodiments, the treatment management and scheduling systems will create a recommended program for a user's next appointment, based on, among other things, the patient's purpose in using the machine, their current medical condition, their historical performance, and aggregate data collected by the system about the performance and progress of other users with similar characteristics. The system may do so by comparing the user's performance data from the last treatment session with aggregated data collected by the system for a population of users. The system may then generate a recommended treatment program for the user's next appointment based on the comparison of the user's information and stats with the data for the population of users.

In some embodiments, the aggregated data may include a performance database based on the demographic and medical data about users and their related workout sessions. This performance database will include and accumulate a qualitative measure from the user about their experience (e.g. pain, satisfaction) during the session. In further embodiments, the aggregated data may include and accumulate data from medical personnel (e.g. physical therapists supervising users) as to the outcome of a user's treatment session. This data will also be stored in the performance database.

In some embodiments, the user may not have any prior experience with the assistive devices or training systems (either DAP or non-DAP unweighting). In such cases, the systems described can design a suitable treatment based on the user's information. For example, a user with no prior DAP system experience may wish to use DAP to improve the user's running speed. To design the appropriate DAP system, the treatment management and scheduling system may receive the user's information regarding the desired treatment result. In this example, the user may input into the treatment and scheduling system that she wants to decrease the time needed for her to run a mile. The user may optionally input additional information regarding her location and the time slot for the treatment. The treatment and scheduling system then employs a predictive algorithm, such as the ones described above, to determine the appropriate treatment and DAP system for the user. The predictive algorithm may compare the user's information to that in a database with aggregate data (including performance data) regarding the population of users that have used a DAP system. The algorithm then assesses the treatment parameters employed by other users to determine what treatment would be suitable for the user. The treatment management and scheduling system may then provide one or more suggested treatments to the user and have the user decide on a treatment.

In the case where multiple treatment options are available, the user may first decide on the type of treatment. Once that is selected, the treatment management and scheduling system may then determine which training system, progression of systems or other rehabilitation equipment can provide that treatment regime. For example, if the algorithm determines that users can improve running speed by modifying gait or by running under positive pressure, the system may offer those two treatment options to the user. If strength or flexibility improvement is needed along with use of the DAP system, for example, then scheduling system can recommend treatments involving multiple modes of therapy. If the user picks gait modification as a treatment, the treatment management and scheduling system may then match the user with DAP systems having gait analysis capability. Alternatively, the treatment management and scheduling system may offer the non-DAP unweighting systems to the user and indicate in the listing that the non-DAP system selected can provide gait or an alternative unweighted treatment.

While the invention herein disclosed has been described by means of specific embodiments and applications thereof, numerous modifications, combinations and variations could be made thereto by those skilled in the art without departing from the scope of the various inventive embodiments and alternatives described herein.

What is claimed is:

1. A method of providing integrated differential air pressure assisted gait training, comprising:
   customizing the integrated differential air pressure system to a user by performing a calibration routine to determine a patient specific calibration factor;
   unweighting the user in the integrated differential air pressure system based on the customizing step;
   performing a therapy routine with the user during the unweighting step;
   collecting under control of the integrated differential air pressure system controller output data from a plurality of components of the integrated differential air pressure system during the unweighting step and the performing step; and
   recommending a user action for gait correction based on one or more of the output data from the collecting step, wherein the user action for gait correction is visible on the display in view to the user during the performing step.

2. The method of claim 1 wherein the output data comprises synthesized data.

3. The method of claim 1 the collecting step further comprising a continuous output data stream, a nearly continuous output data stream, a segmented output data stream, or a synthesized output data stream from the integrated differential air pressure system.

4. The method of claim 1 further comprising storing the output data in a database.

5. The method of claim 4 wherein the database contains DAP and gait system data corresponding to a user's progress through a continuum of care.

6. The method of claim 5 wherein the continuum of care ranges from immobile, to partially mobile, to fully mobile.

7. The method of claim 6 further comprising comparing the data to data from a device in another segment of the continuum of care.

8. The method of claim 7 wherein the data from a device from another segment is gait data collected from a leg worn actuator.

9. The method of claim 7 wherein the data is gait data collected from a full mobility measurement system.

10. The method of claim 1 wherein the recommending step permits connection of an alteration of a parameter of the differential air pressure system or user gait change to a real time feedback.

11. The method of claim 1 wherein the step of collecting output data from the plurality of components includes an instrumented article worn by the user.

12. The method of claim 11 wherein the instrumented article worn by the user is within a pressurized chamber of the integrated differential air pressure system during the performing step and the collecting step.

13. The method of claim 12 wherein the output data collected from the instrumented article worn by the user during the collecting step includes data about a hip position of the user.

14. The method of claim 12 wherein the instrumented article worn by the user is a shoe.

15. The method of claim 12 wherein the instrumented article worn by the user is a garment.

16. The method of claim 1 further comprising: storing the user action for gait correction with the output data of the collecting step.

17. The method of claim 16 wherein the user action for gait correction is related to a correction of a user foot strike force asymmetry, a user stride, a user cadence asymmetry, or a user body phase coordination.

18. The method of claim 1 further comprising initiating capture of a video image of the user using a trigger provided by at least one of the plurality of components of the collecting step.

19. The method of claim 1 wherein a trigger provided by at least one of the plurality of components of the collecting step is provided by a sensor worn by the user.

20. The method of claim 1 wherein a trigger provided by at least one of the plurality of components of the collecting step is provided by a sensor of the integrated differential air pressure system to detect an impact of the user foot with a treadmill within the integrated differential air pressure system.

21. The method of claim 1 the recommending step further comprising:
providing a recommendation to decrease the amount of unweighting provided by the integrated differential air pressure system.

22. The method of claim 1 further comprising: storing data from a sensor worn by the user during the performing step; and
synchronizing the data from the sensor to the output data collected during the unweighting step and the performing step.

23. The method of claim 22 wherein the synchronizing step is done during the performing step.

24. The method of claim 22 wherein the synchronizing step is done after completion of the performing step.

25. The method of claim 22 wherein the sensor worn by the user is within a shoe worn by the user.

26. The method of claim 1, the collecting step further comprising: wirelessly receiving output data from one component of the plurality of components.

27. The method of claim 1 wherein the user action for gait correction visible on the display includes a graphic indication of a detected asymmetry.

28. The method of claim 27 wherein the detected asymmetry is a differential air pressure assisted force asymmetry.

29. The method of claim 27 wherein the detected asymmetry is a differential air pressure assisted cadence asymmetry.

30. The method of claim 1 wherein the user action for gait correction visible on the display is a recommended adjustment to the level of differential air pressure unweighting provided by the integrated differential air pressure system.

31. The method of claim 1 wherein the display is within reach of the user during the performing step and the collecting step.

32. The method of claim 1 wherein the user action for gait correction visible on the display includes a pictogram of at least one of stepping performance, upper body phase coordination, cadence, left/right stride length, left/right stride time, stride length, heel strike, knee bend, foot placement phase asymmetry, and stride time jitter.

* * * * *